United States Patent [19]

Gilford

[11] 4,058,367

[45] Nov. 15, 1977

[54] AUTOMATIC ASYNCHRONOUS FLUID PROCESSING APPARATUS

[75] Inventor: Saul R. Gilford, Oberlin, Ohio

[73] Assignee: Gilford Instrument Laboratories Inc., Oberlin, Ohio

[21] Appl. No.: 715,661

[22] Filed: Aug. 19, 1976

Related U.S. Application Data

[63] Continuation-in-part of Ser. No. 578,872, May 19, 1976, abandoned, which is a continuation-in-part of Ser. No. 428,803, Dec. 27, 1973, abandoned.

[51] Int. Cl.² .......................... G01N 1/14; G01N 33/16
[52] U.S. Cl. .................................... 23/253 R; 23/259; 364/416
[58] Field of Search ............... 23/253 R, 259, 230 B, 23/230 R; 141/130; 235/151.12, 151.35; 73/425.4 R, 425.6

[56] References Cited

U.S. PATENT DOCUMENTS

| | | | |
|---|---|---|---|
| 3,476,515 | 11/1969 | Johnson et al. | 23/253 X |
| 3,497,320 | 2/1970 | Blackburn et al. | 23/253 X |
| 3,597,161 | 8/1971 | Greiner | 23/253 R |
| 3,660,638 | 5/1972 | Oberli | 23/253 R |
| 3,728,080 | 4/1973 | Moran | 23/253 R |
| 3,770,382 | 4/1973 | Carter et al. | 23/253 R |
| 3,799,744 | 3/1974 | Jones | 23/259 X |

Primary Examiner—R.E. Serwin
Attorney, Agent, or Firm—Baldwin, Egan, Walling & Fetzer

[57] ABSTRACT

Apparatus for processing fluids such as blood or the like for ascertaining physical and/or chemical properties thereof. Samples to be processed are contained in disposable containers and moved to different zones where various functions are performed such as adding reagent, incubating, testing, reading out data and discarding the container. The movement of the containers is afforded by a carriage moving on a guideway and having reciprocating embodiment, the containers each carry indicia means identifying the sample and including a test code prescribing a particular test procedure which is to be followed by the apparatus. In another embodiment it is intended that identification of the patient's sample will be initially made on the container which initially receives the sample and thereafter as portions are dispensed from said container for use in processes this identity will be accomplished by suitable computer means. The apparatus includes programming and control means in the form of computer circuitry including memory storage. The instructions on test procedure are stored in the memory along with information on the location of the carriage along the guideway at all times, the location of sample containers along the guideway and the amount of time that any sample container has been delayed. The enabling signals for operation of the apparatus may be produced by the programming and control means which is arranged to provide for time sharing.

Typically, if, during the processing of a sample in a container the delay time is sufficient to start or complete another sample test, the carriage is operated to pick up another container from the supply means and start processing it, or complete the processing of a container and sample which had previously been started. The program and control means, through its memory, adjust the operations of the carriage so that it is performing some function at practically all times thereby using the apparatus most efficiently as to time.

The operation of the apparatus is asynchronous in that there is no continuous predetermined movement of any elements without regard to the individual requirements of the test procedures and there is no continuous cycling of any components. Movements and functions are performed only as needed and only for the times needed.

The apparatus may include multiple reagent adding positions in the reagent adding zone; multiple incubating positions with different available times and temperatures in the storage zone; multiple individual testing apparatus available at the testing zone; a combined readout and disposal means for the containers and their identification cards or a combined readout and card-removal means with separate container disposal means.

Conveniently there may be two carriages on the same guideway responding in cooperation to perform the needed functions of the processing, overlapping in travel extent, but both controlled so that there is no interference between them.

63 Claims, 12 Drawing Figures

AUTOMATIC ASYNCHRONOUS FLUID PROCESSING APPARATUS

This application is a continuation-in-part of my application Ser. No. 578,872, filed May 19, 1976 entitled "Automatic Asynchronous Fluid Processing Apparatus", now abandoned, which is a continuation-in-part of my application Ser. No. 428,803, filed Dec. 27, 1973, entitled "Automatic Asynchronous Fluid Processing Apparatus", now abandoned.

BACKGROUND OF THE INVENTION

The invention relates to automatic analyzing apparatus in which a liquid sample is to be tested, usually chemically, and the results of the test related to the identity of the liquid sample.

The invention herein is primarily related to the testing of biological samples such as blood, but is not so limited.

Diagnosis, preventative medicine and information concerning the efficacy of treatment are greatly aided in modern medical practice by making a myriad of tests on blood. These tests may be divided into two major categories, physical and chemical. The physical tests are accomplished by operating on the whole blood and the chemical tests are performed by operating on the blood serum, that is, the liquid which remains after the blood cells have been separated therefrom.

The physical tests include counting and sizing the white and red cells, measuring the prothrombin time of the blood, measuring the hematocrit, etc.

The chemical tests are performed by adding certain reagents to the serum, subjecting the resulting solution to certain temperatures for particular times and then making colorimetric measurements of absorbence of certain monochromatic light. In some tests, the solution is sprayed into a flame and the resulting color is measured. In some tests reactions are measured at intervals to give dynamic data.

The information which can be obtained by means of tests of the chemical type include ascertaining the quantitative amounts of organic and inorganic substances in the blood, turbidity with respect to certain substances, etc. Some of these tests are identified as follows:

cholesterol
protein
chloride radical
urea
uric acid
bilirubin
sugar
calcium
sodium
enzymes of different kinds
gamma globulin
various organic acids
hemoglobin and many others.

The invention is primarily directed to novel apparatus for making chemical tests, but as will be pointed out, physical tests can be made as well. In such cases, the sample prepared from whole blood is not necessarily centrifuged, but will be diluted and, if necessary lysed. The diluted sample can be automatically passed to a cell counting and sizing apparatus for making a determination of the red blood cell population and/or a lysed diluted sample can be automatically passed to such apparatus for determination of the white blood cell population.

The chemical tests are normally made by adding a reagent to a serum sample, incubating it for a given time at a given temperature and then measuring the absorbency of the sample with respect to monochromatic light passed through the same. Apparatus are available, and such are contemplated by the invention, in which there is a dip tube or snorkel which may be automatically dipped into a sample container, sucks a quantity of the sample into a test cuvette, projects light from a spectrophotometer comprising part of the apparatus through the cuvette and reads out the absorbency in absorbence units by means by suitable photoresponsive means and electrical circuitry converting the electrical output of the photoresponsive means into a signal that has been logarithmically operated upon by the circuit to give a linear response. The wave length of the incident light is adjusted by the operator prior to setting the apparatus in operation, but this can be done automatically as described hereinafter.

The apparatus of the invention is an automatic analyzing device in which a plurality of samples is passed through the machine and each sample is tested and the results are provided as one of the outputs of the device.

Such apparatus, per se, is well known but the nature and characteristics of such known apparatus have inherent disadvantages which the invention herein obviates. Ultimately, the ends sought by the invention herein are greater reliability, economy, simplicity and a higher throughout than prior machines, even those which are much larger and more sophisticated than that to be described and claimed. The manner in which these ends are accomplished is inherent in the structure and method of operation of the apparatus of the invention which differs considerably from that which is known as will be apparent.

To understand and appreciate the invention, it will be valuable to discuss the structure and operation of automatic analyzing apparatus which are known at the present time.

Known apparatus are of the so-called single channel and multiple channel variety. This designation "channel" is used to signify a test which is being run. Thus, a single channel apparatus will handle a single sample and will perfrom one test on that sample. The operator feeds a plurality of samples in suitable containers to the machine and the machine moves the samples through the procedure which has been established, either by the construction of the apparatus or by adjustments made thereto, and the output of the machine comprises the results of these tests produced by the apparatus one at a time.

Multiple channel machines use a single sample which is transferred to a plurality of reaction vessels and the respective reaction vessels go through individual tests and provide a plurality of test results each of which is independent of the other but all of which are related to a single sample.

In each of the above apparatus there are variations. Some apparatus provide means for handling different tests in a single channel machine so that each sample fed to the machine will be tested in a different manner. For example, a package of reagents may be furnished for any one of a large number of tests and the machine automatically constructed to run the test which is chosen by the operator with the package automatically running through the test and producing the desired results. Any other single channel machine must be changed in its operation in case it is desired to change the test from the current one being run to another.

As for the multiple channel devices, some give test choices by eliminating selected ones of the entire apparatus repertoire; some require all tests to be performed on all samples regardless of need.

All of the above machines have a characteristic which is wasteful of time and wasteful of the capability of automatic apparatus. This is the fact that the sample is transported through the machine and the test performed at a speed which is fixed by the construction of the machine. The speed is determined by the time that is required for the longest test to be made. The samples and/or reaction vessels are moved through these machines on belts, chains, wheels, or through tubes at a constant rate. If a reaction is to require more time than another, the first reaction is started earlier along the path of movement so that all testing is done at a single location.

The functions which are to be performed in these automatic machines include adding reagents to the samples, incubating, mixing, transferring treated samples to colorimeters, etc. Added to these functions, in multiple channel machines which use reaction vessels, the vessels have to be washed, rinsed and returned to the beginning of a path of movement.

The principal difference between the present apparatus and those of the prior art, as will be appreciated from the detailed description which follows, is that the present apparatus operates asynchronously. There is no preset cycle of operations which must be followed by every sample; no continuously moving chain or belt or series of racks; no specific order of processing the samples; and no handling and/or recycling of the same reagent containers or vessels. Each sample is tested individually on a shared time basis, the apparatus operating asynchronously and automatically in that said sample follows a predetermined procedure, which if it includes any delay, enables the apparatus to be gainfully occupied during the course of such delay. An important structure provided by such apparatus is a carriage or pair of carriages moving along a guideway and engaged in handling the sample containers throughout their testing procedures. The carriages pick up the samples and carry them to the appropriate zones where functions are performed, depositing them where required in storage zones for incubation at ambient or other temperatures for predetermined times. If the delay or delays resulting are substantial, the apparatus remembers the position of deposit, times the length of resulting delay and while such time is passing performs other functions. For example, a carriage may return to the initial zone where it picks up another sample, enters its code into the memory of the program and control mechanism, moves the sample container to the reagent-adding zone where it adds a totally different reagent or the same reagent as in the first sample, and then deposits this second container in another position of the storage zone — again remembering the location of the deposit and the time required. If in the meantime the time for the first sample to have been incubated has been used up, one or the other of the carriages will move to the storage zone, pick up the first sample container, carry it to the testing zone where it will be tested and generally move it through the procedure which has been predetermined for it. The said procedure is predetermined and programmed by suitable instructions which have been electronically stored in the memory of the programming and control device and coded to the test code carried on indicia means attached to the particular sample container.

One can visualize the apparatus of the invention in operation as a machine which includes one or more carriages rapidly moving back and forth along a guideway carrying out multiple testing of a plurality of samples in respective sample containers. The containers are picked up and moved and deposited in accordance with procedures which overlap and are intermixed in time so that there is no continuous or cyclical movement. The equivalent would be an infallible chemist with a prodigious memory, or two such chemists with their memories connected in the case of an apparatus having two carriages, scurrying back and forth, picking up samples, processing them, remembering where they are and how long they are to be there, testing the, recording results, etc., all intermixed by properly timed in accordance with procedures for the test codes that the infallible chemists have together memorized. No time is wasted, no delay permitting other processing is permitted to pass, and everything is done efficiently and with complete identification as a result of which the maximum number of tests is done in the minimum of time but with the least amount of apparatus.

DESCRIPTION OF THE PRIOR ART

Typical patents of the prior art showing the type of automated processing apparatus which has been mentioned above and giving rise to the enumerated and other disadvantages are:

| | |
|---|---|
| Moran | 3,622,279 |
| Netheler, et al. | 3,644,095 |
| Natelson | 3,260,413 |
| Matte | 3,617,222 |
| Heinz et al. | 3,589,867 |
| Gilford | 3,526,125 |
| Bednar et al. | 3,504,376 |
| Buckle et al. | 3,489,521 |
| Wasilewski | 3,432,271 |

The U.S. patents mentioned have not all resulted in commercial apparatus, and even such apparatus that has resulted has not been totally successful.

In the course of detailing the preferred embodiments of the invention, mention will be made of structures which are disclosed in other patents owned by the assignee of this application, such patents comprising:

| | |
|---|---|
| Gilford | 3,475,127 |
| Gilford | 3,647,386 |
| Gilford | 3,645,252 |
| Gilford, et al. | 3,344,702 |

SUMMARY OF THE INVENTION

Automatic asynchronous apparatus for processing fluids such as blood and the like for obtaining information relating to the physical and/or chemical properties thereof. The invention provides a plurality of zones along a guideway upon which a carriage is arranged to move. There is a first zone in which sample containers may be individually extracted from a supply of the same, each container preferably being disposable and having sample identification and test code information on suitable indicia means such as, for example, a printed card containing both machine and human readable markings. The first zone also has means for electronically reading the test code of any sample container which is extracted, the carriage having structure for enabling the extraction of a sample container from positions in the several zones or the insertion of said container into positions of the several zones.

A second zone has means for adding reagent to sample containers through a suitable access opening in the container; a third zone has storage stations in which sample containers may be deposited for incubation at controlled temperature for certain prescribed lengths of time; a fourth zone has means for extracting fluid from the sample container through another or the same access opening and moving the fluid through a testing device. Each zone may have multiple positions, as for example, there may be several testing machines so that the fourth zone has a position corresponding to each machine at which fluid can be withdrawn. A fifth location along the guideway may provide a readout device and at this point the indicia means of the sample container is read and identified with respect to data which has been generated for that sample in a testing machine. The data may be printed on the indicia means or transmitted elsewhere or recorded in an identifiable manner on a suitable document. The indicia means may be separated from the container at this point and stored or the container and indicia means may be passed to a following station where the separation is effected and the containers disposed of in one manner and the indicia means in another.

The apparatus includes programming and control means including a memory, the programming and control means furnishing the energizing or enabling signals which operate the apparatus, including, for example, signals to cause the transport means to drive the carriage to various locations along the guideway, signals which cause the operation of the sample container reciprocating device in extracting or inserting the containers relative to the positions of the respective zones, etc. The movement of the sample containers may energize or enable the operation of components or the programming and control means may effect such operation in concert with movement of the containers. Thus, for example, the movement of the container into a position of the second zone may trip a switch to start the cycle of a reagent pump which will feed reagent into a nozzle engaged in the access opening of the container; while on the other hand, the positioning of the carriage at a particular location with respect to the third zone may bring about the production of an enabling signal directed to the particular testing machine from the programming and control means, this latter signal originating in the last-mentioned means.

The overall operation of the apparatus is tied in with the memory which, in addition to previously inserted instructions for testing procedure individual to the respective test codes, carries temporarily information concerning the location of the carriage, the location of specific sample containers being incubated and the time they are to be so incubated, the arrangement of a carousel of sample containers or a cassette of the same, etc.

The programming and control means are arranged to utilize the time of the processing in the most efficient manner by sharing time, in a way of speaking. Where a procedure required delay, as for example, in the case that a sample container is stored in the storage zone to incubate or permit a reaction to occur over a period of time, obviously since the guideway is capable of being used in the meantime, the carriage is directed to process other samples. Thus, it may move to the first zone, pick up a second sample container, move it to the reagent-adding zone and add reagent from the same or a different reagent nozzle, and then move it to a second position in the storage zone to incubate it. Following this, the carriage may go back to the first position of the storage zone where the first sample container had been left, and assuming that the incubation time of that first sample container is completed, pick up the first sample container and carry on to the remainder of the testing procedure. The information concerning its deposit of the second sample container is still in the memory, and when the incubation time for the second sample container has been completed, the carriage will go to that position, pick it up and continue with the test procedure for that particular sample.

Thus, multiple sample containers are simultaneously being processed, but in an orderly fashion with respect to their particular procedures as called for by the individual test code carried on the indicia means of the respective sample containers, and with overlapping time periods. The total time required to complete a single test procedure is shared by other test procedures to the extent that delays in any one or more procedure permits the operation of the carriage.

In a more sophisticated version, there are two carriages arranged on the same guideway, their extent of travel overlapping, but synchronized so as not to interfere with one another. The programming and control means can command the one carriage to perform functions which have been started by another in the event that the latter carriage is occupied when a step of the procedure must be performed and there is a length of guideway that is free over which the one carriage can travel. The time sharing for the performance of parts of procedures simultaneously and the cooperative functioning of the two carriages can readily be programmed in the programming and control device, this latter apparatus being practically a computer.

BRIEF DESCRIPTION OF THE DRAWINGS

FIG. 9 is a partial view in perspective of a process or serum cup magazine and dispensing device constructed in accordance with its intended environmental use herein;

FIG. 10 is a partial view in perspective of sample supply, dispensing and carriage mechanism;

FIG. 11 is a partial view in perspective of the sample supply and dispensing mechanism as illustrated in FIG. 10; and FIG. 12 is a partial view in perspective of apparatus for temporary incubation of serum samples.

DESCRIPTION OF THE PREFERRED EMBODIEMNTS

Figure 1:
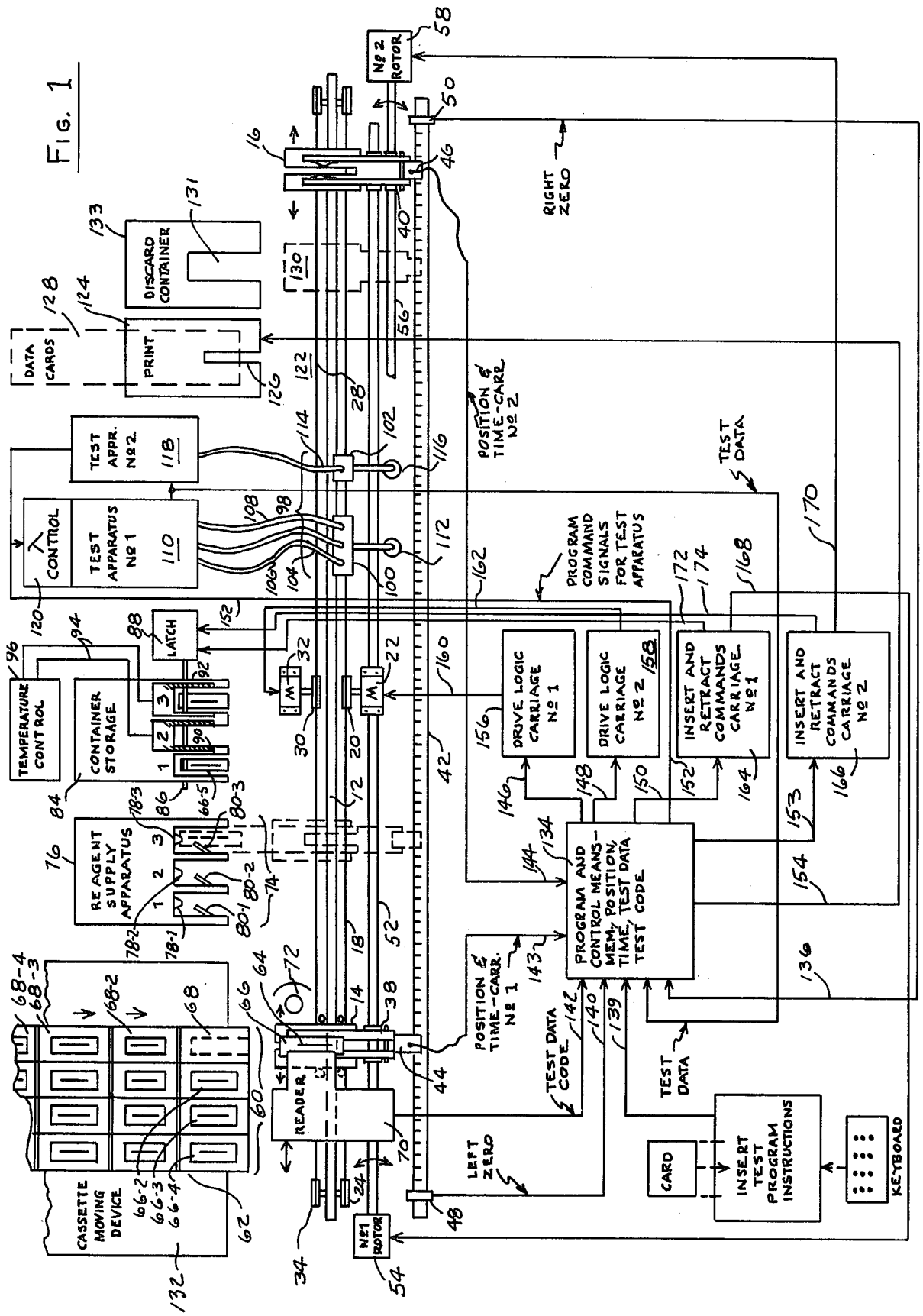
FIG. 1 is a diagrammatic view of apparatus constructed in accordance with the invention, the view including simplified blocks and symbols in place of the actual components, the construction of much of the latter being known.

The invention is embodied in a system which is capable of relatively wide variation in its components and the arrangement thereof, but there are certain basic features which all versions of the invention will have in common. These are the following:

1. The apparatus contemplates that there will be samples carried in containers and having some means for identifying the samples and the tests which are to performed thereon;
2. The apparatus contemplates that there will be a zone at which a supply of these containers will be available, capable of being extracted at said zone to be moved into the flow path of the apparatus for processing, there being a code reading device as close to the zone as feasible to identify the test code printed on the identification card (indicia means) that is carried by the container;
3. The apparatus contemplates that there will be a carriage that is capable of being driven back and forth along a guideway from one end to the other, the carriage having a reciprocating holder for a sample container, the holder being capable of picking up or depositing the sample container;
4. The apparatus contemplates that there will be a plurality of processing zones along the path of movement of the carriage including a reagent-adding zone and a testing zone, the carriage being arranged to move the positions of these zones as commanded by the test procedure for the particular sample and to reciprocate the sample container into association with the apparatus at these zones if necessary in order; to accomplish the functions which they admit of;
5. The apparatus contemplates that there will be a readout station and perhaps a discard container device at the same station at which point the card of the container is electronically read so that the test data generated may in some manner be recorded; and
6. Finally, the apparatus contemplates circuitry and associated electrical and mechanical means to coordinate the operation of the apparatus in the manner described. There is required program and control means including a memory for permanent and temporary storage of information. The latter means are required to generate the signals needed to drive the carriage to various places along the guideway; to receive and store information concerning the location of the carriage translated into information concerning the location of sample container positions and the time for which the containers have remained at the respective locations as well as the time which is left at which they should remain at the locations; to receive and store information concerning the test procedures to be followed related to particular respective test codes; to generate signals for reciprocating the holder for deposit or extraction of sample containers; to generate signals for operation of the test apparatus, readout apparatus, container discard apparatus; to carry out the respective test procedures in the minimum amount of time, irrespective of whether this same time was required for other samples being tested.

It is pointed out that one important feature has been omitted from the above list of features, that being means to store sample containers at a storage zone while they are being incubated or in some manner delayed. Most if not all systems will have such a storage zone and most if not all systems will also have multiple positions at the reagent-adding zone at which different reagents can be added to different sample containers, so that the respective test procedures will call for different reaction times.

Although to some extent the apparatus which excludes multiple storage positions and multiple reagent-adding positions might be considered unusual, it is not totally impractical. Nonetheless, the basic concept of the apparatus is emphasized with the minimum number of required elements recited above by pointing out that the apparatus is constructed and arranged to perform the test procedure in the minimum of time possible, regardless of the time occupied by the other procedures.

For example, if the reagent-adding zone has only one dispensing nozzle but one test requires more of the identical reagent than another, even assuming that there is no storage zone, the sample container will be disposed at the dispensing nozzle longer for the one test than the other. In prior art apparatus, so far as known, the time cycle of the apparatus would have to be adjusted so that the processing time for all tests is the same, regardless of how long the sample container remains at the dispensing nozzle. In the apparatus of the invention, the programming and control means will use less time to complete the test procedure for that procedure using the lesser amount of reagent because the sample container remains at that position less time.

As mentioned, the practical version of the invention will have the storage zone with positions providing different incubating temperatures and perhaps including some with no temperature control at all — where the delayed sample container is permitted to remain at ambient temperature for a period of time to permit a reaction to occur. Also, such practical version will normally have means for dispensing several different kinds of reagent for different tests.

The apparatus of the invention is capable of handling samples requiring widely divergent testing procedures on a random order and will utilize the time involved in carrying out such procedures with the maximum of efficiency.

Mixing, agitating and the like means will normally be provided in a practical device.

In FIG. 1 the overall apparatus is designated generally by the reference character 10 and the mechanical and electrical apparatus are shown in highly simplified diagrams above with the electrical circuitry for the most part in block form shown below. The apparatus 10 comprises a guideway 12 which may be a rod having a left-hand carriage (No. 1) 14 mounted thereon for right and left movement confined by said guideway 12 and a right-hand carriage (No. 2) 16 mounted thereon for right and left movement also confined by said guideway 12. A practical design for such carriage as 14 or 16 is detailed in FIGS. 4 and 5. As will be seen hereinafter, each carriage has a roller which engages on a track for assisting in the carriage movement, this not being shown in FIG. 1. The left carriage 14 has the ends of a wire loop 18 connected thereto, the wire loop being frictionally engaged around the pulley 20 of the drive motor 22 and passing over end pulleys 24 and 26 mounted to a support (not shown in FIG. 1) for the apparatus. The right carriage 16 has the ends of the wire loop 28 connected thereto, the wire loop being frictionally engaged around the pulley 30 of the drive motor 32 and passing over the end pulleys 34 and 36.

Each carriage has a container reciprocating device designated generally 38 and 40 in FIG. 1 which is designed to pick up or extract a sample container from a position alongside the guideway 12 or deposit such container in a suitable position. In addition, when a container has been picked up by the device 38 or 40, it is retained on the device and hence can be moved with the carriage. The apparatus has an elongate scale 42 spaced from and parallel with the guideway 12, the scale being provided with equally spaced segments that can be identified by suitable electronic and/or optical means indicated generally at 44 and 46, the latter being carried by the respective carriages 14 and 16. For example, there could be a series of slots in the scale 42 with a lamp and photoresponsive device carried by each carriage straddling opposite sides of the scale so that there is a signal produced in the photoresponsive device each time a slot is passed. In this way, information in the form of signals can be generated which identifies the exact location of each carriage at all times by reason of the number of slots passed and the direction occurring in movement along the guideway 12 and the scale 42. End reference members are mounted on the scale 42 at 48 and 50 to provide end left and right zero reference signals, respectively.

The left carriage 14 has a square shaft 52 passing through a square opening in its reciprocating device 38 so that rotation of the shaft 52 by the electrically operated rotating means 54 (No. 1 Rotor) will operate the said device 38. Another square shaft 56 (shown broken away) passes through a clearance hole in the carriage 14 and engages a square or otherwise confining hole in the reciprocating device 40 of the right carriage 16 so that rotation of the shaft 56 by the electrically operated rotating means 58 (No. 2 Rotor) will operate the said device 40. The carriage 16 has a clearance hole through which the shaft 52 passes so that rotation thereof will be freely permitted.

The apparatus 10 includes multiple zones where functions related to the operation of the apparatus are located alongside of the guideway 12. At the left there is an initial indicia means reading zone 60 within which two functions normally are performed. These functions, detailed hereinafter, comprise withdrawing sample containers from some form of sample supply means 62 and disposing it onto the carriage 14 and reading the test code carried by the identification card 64 that is on the container. One container 66 is shown on the carriage 14, but the details thereof will be described. Other containers are shown at 66-2, 66-3 and 66-4 in a cassette 68 of the sample supply means 62.

The reading is carried out by an optical-electronic reader 70 that responds to, for example, the light from the lamp 72 passing through the machine-readable code holes punched in the card 64 and designating the test code. The reader 70 is movable to a limited extent left and right as will be explained.

The second zone 74 is the reagent-adding zone and in FIG. 1 there is shown reagent supply apparatus 76 having three positions suitably numbered, each having a dispensing nozzle as at 78-1, 78-2 and 78-3 adapted to dispense specific volumes of different reagents. Each position has a leaf switch, the actuating element of which is shown symbolically at 80-1, 80-2 and 80-3 respectively, so that when a sample container such as 66 is moved into a position by the reciprocating device 38 (see phantom outline in FIG. 1), the depression of the element such as 80-3 will start the dispensing cycle. The container will be in position so that the nozzle such as 78-2 enters an access opening. When the dispensing cycle has been completed, the container such as 66 is retracted onto the carriage 14.

The third zone is a container storage zone 82. As shown in FIG. 1, there is a container storage device 84 which is actually intended for incubating purposes. Shown are three positions or stalls each having means to engage and hold a sample container therein, including a latch bar or shaft 86 operated by a latch drive mechanism 88. As will be explained, the latch bar 86 cooperates with a tooth on the respective sample containers. In the stall marked 1, the walls are shown with no means for heating the stall. A sample container, such as that shown at 66-5, placed in this stall will remain there at the ambient temperature. If, for example, it requires a period of time for a reaction to occur after some reagent has been added to the sample contained within the sample container, and without changing the temperature thereof, the container could be placed in the unheated stall No. 1. Stalls No. 2 and No. 3 have heating elements as indicated at 90 and 92 connected by the lines 94 to a temperature control device 96. These stalls may be maintained at the same or different temperatures. Note that a sample container 66-6 is shown in stall No. 3.

The fourth zone which is illustrated is at 98 and it comprises the testing zone. Here there are either several positions to which the sample containers may be moved and where sample may be withdrawn from them by snorkel means, for example, or the zone may comprise a location along the guideway where snorkel means may be provided for movement into and out of the sample containers without the need for operating the reciprocating device.

The zone 98 has snorkel holding brackets at 100 and 102, the bracket 100 having three snorkels 104, 106 and 108 leading to a test apparatus 110 designated Test Apparatus No. 1. The bracket 100 is adapted to be raised and lowered by a plunger 112 operated in synchronism with the operation of the test apparatus 110 by some mechanism which is not shown. Likewise, the bracket 102 has a snorkel 114 which can be raised and lowered by the plunger 116 operated in synchronism with the operation of the test apparatus 118, the latter being designated Test Apparatus No. 2.

The test apparatus 110 could be a plurality of spectrophotometers operating independently and each having a wave length control such as shown at 120 or it could be a spectrophotometer which is intended to make dynamic enzyme measurements including a cuvette moving device and suitable apparatus for making a multiple determination of the type disclosed in U.S. Pat. No. 3,344,702. The test apparatus 118 could be a duplicate of apparatus 110 for increasing the throughput of the apparatus or it could be other testing means such as for example, electronic blood cell or particle counting apparatus.

The next location along the guideway 12 is the final indicia means reading station 122 at which there is disposed a readout or recording device 124. In FIG. 1 this is designated "Print" it being contemplated that in a preferred embodiment, the carriage 14 (or 16) will bring a sample container to the station 122, will move the container laterally of the guideway 12 so that its card such as 64 will enter the slot 126 where it will be identified and related to information which has been derived from one of the testing apparatus 110 or 118. The results of the test will be printed on the same card and the card may be removed for retention by suitable apparatus such as indicated by the phantom line block 128. If this arrangement is not used, after recording the information on a suitable record, the sample container is retracted from the slot 126 back onto the carriage and the carriage moves to a further station 130 at which the sample container may be moved off the carriage into a slot 131 of the discard apparatus 133 from which the container and card may be disposed of.

Adverting now to the left-hand side of FIG. 1, the sample supply means 62 is here shown as an array of cassettes 68 each of which contains four sample containers. Actually the cassettes more conveniently will contain ten or more such samples and will be prepared by the technicians from samples gathered and identified. These cassettes can be stacked or otherwise arranged in rows in a moving device 132 which mechanically moves a cassette forward to the position occupied by the bottommost one when that one has been depleted and moved out of position. Thus, the cassette marked 68 will move to the right in FIG. 1 and the following cassettes 68-2, 68-3, etc. will move down. The programming and control means represented by the block 134 may be connected to drive means of the cassette moving device to synchronize movement of the device 132 with the removal of sample containers. The connecting lines or channels are not shown in the view. There can alternately or in addition be sensing means operating by virtue of the movement of the sample containers themselves to accomplish the functions of moving the cassettes into their desired positions.

As previously mentioned, it is contemplated that the reader 70 will move to the left each time that a sample container has been removed from the bottommost cassette 68. There could just as well be some means which senses when the last sample container, for example 66-4 has been removed from its cassette, this signal being utilized to return the reader 70 to its right-hand position for being aligned with the right-handmost sample container of the next following cassette. Also, this same signal could be used to operate the device 132 to discard the empty cassette and bring into position the next cassette.

A well-known expedient found in many prior art automated apparatus for feeding sample containers to the moving belt or chains of the system is a carousel. Such carousels are also used to transfer samples from sample containers to the permanent reaction vessels carried by the chains or belts wherein the mixing and reactions occur. The invention herein can use a carousel at the zone 60 in place of the cassette arrangement which has been illustrated and described, the carousel adapted to be loaded manually or in some semi-automatic manner with sample containers like those shown at 66, each having an identifying card. In such case, the carousel will rotate an increment each time that a sample container has been removed and there is no need for movement of the reader 70. Also in such case, obviously, the zone 60 will comprise a single position.

Reference may now be had to the lower portion of FIG. 1 which illustrates principally the electrical circuitry and associated channels of the apparatus 10.

As stated, there is a central command station which is designated program and control means 134 which includes a memory. The program and control means comprise principally, if not exclusively, electrical circuitry and possibly switching means, timing means and the like. The memory is capable of storing and having called up therefrom permanent and temporary data. This storage means or memory need not be extensive, but may still have the capability of handling a substantial volume of tests.

The best way of following and understanding the operation of the apparatus 10 is to consider the lines or channels which are coupled with the program and control means 134. Inputs are shown at the top and left while outputs are shown at the bottom and right. It is to be appreciated that the program and control means 134 is not self-actuated and timed as is the case with much of the prior art. Instead, its operation depends upon information supplied to it, and the programming is a result of accommodation to this information. The device 134 may be considered a computer and, indeed, computations are made for the proper timing and interrelation of the several functions which are commanded thereby.

Starting with the lower left-hand corner of the block 134, the channels or lines are designated in a clockwise direction 136, 138, 139, 140, 142, 143, 144 for inputs; and 146, 148, 150, 152, 153, and 154 for outputs. Since the lines and channels described are only by way of example, there may be more or less than those specifically illustrated depending upon the functions required of the apparatus.

The memory store of the program and control means 134 may have a limited capacity, as explained. Nevertheless, it is capable of handling a great variety of tests. At 156 there is shown a block which is in the form of a terminal connected to the program and control means 134 by the channel 138. This could be a large number of lines to enable rapid transmittal of information into the memory of the program and control means 134. The block 156 enables test information to be stored in the memory. It is designated Insert Test Program Instructions. Through the use of magnetic cards such as 158 or a keyboard 160 the inserting terminal 156 will store in the memory complete test instructions for several test procedures which the apparatus 10 is required to follow. These instructions are of a permanent nature in that they will remain in the memory until erased therefrom. Thus, if it is known that the apparatus 10 is to perform certain tests for a period of time, all previous test information can be erased by the insert terminal 156 and only those which are desired inserted. In this manner, the memory of the program and control means 134 need not be too extensive.

The instructions stored and relating to the test procedures are stored with call-up information in the form of a test code. Thus, when a test code corresponding to a particular procedure appears on the card 64 of a sample container 66 and is read by the reader 70, that information is transmitted to the program and control means 134 by the line or channel 140 after which the procedure is followed by the programming portion to cause the called-for functions to be performed by the apparatus.

The temporary information which is stored in the memory of the program and control means 134 appears on the other input lines. The positions of the carriages 14 and 16 are represented by the information appearing on the lines 143 and 144, being derived from the structures 44 and 46 working in conjunction with the scale 42 and its slots mentioned above. In order to have a point of reference at each end of the scale, there are zero stops at 48 and 50 which transmit reference signals to the program and control means 134 by way of the input lines 136 and 142. The call-up of the test procedure information from the reader upon reading a particular test code is effected by way of the line 140. When a test has been performed, the test data may be stored temporarily in the memory or may alternately or in addition be immediately transferred to the printer 124. The channel from the testing apparatus such as 110 and 118 is shown at 139, and it should be understood that this channel will usually comprise a plurality of conductors.

With respect to outputs, the various functions which are performed are achieved by way of several circuits which may include mechanical devices, switches and the like, in response to the commands of the program and control means 134.

The movement of the carriages 14 and 16 is effected by driving the motors 22 and 32 in the appropriate direction and for the appropriate time. The two outputs 146 and 148 accomplish this through logic circuits 156 and 158 connected to the motors by way of the lines 160 and 162, respectively.

The movement of the carriages can be at high speed using known arrangements. The reciprocating devices 38 and 40 of the carriages 14 and 16 respectively are operated by rotors 54 and 58 as explained. These latter rotors are energized by suitable logic circuits 164 and 166 by way of the lines 168 and 170, respectively in response to commands appearing on the lines 150 and 153. When sample containers are to be retracted from locations where they have been stored, as for example, if stored in the container storage means 84, they must be released by the structure at that location which has been holding them in position. In the case of the container storage means 84 it was explained that there is a latching bar 86 which holds the containers. Thus, when the program and control means 134 calls for the container to be picked up from such a position, in addition to the reciprocating device of the particular carriage being required to move forward, the latch must be released by operation of the latch or unlatch mechanism 88. The same logic circuits 164 and 166 can provide such command signals because they must occur in synchronism with the reciprocating signals. The pertinent connections are designated 172 and 174 in FIG. 1.

The other output lines which are shown are the lines 152 and 154. The first of these provides the command signals for operating the test apparatus when a sample container such as 66 is in position at the zone 98 and the second of these energizes the print apparatus 124. Variations in the method of achieving the desired functions will occur to those familiar with this art, for example, being related to the arrival of a carriage at a certain position and the existence of sensors at that position to detect such arrival and provide the necessary command signals in lieu of or in addition to command signals furnished by the program and control means.

The use of two carriages such as 14 and 16 is a refinement of the basic invention as originally conceived intended for increasing the speed of operation of the apparatus. It is clear that the program and control means 134 is required continuously to monitor information as to the location of the two carriages, continuously to test the conditions under which one or the other of the carriages is better able to perform a given function and continuously to maintain a separation of the command signals driving the carriages so that they do not run into one another while still being able freely to overlap one another's positions along the guideway. In order to explain the manner in which apparatus such as shown in FIG. 1 operates with only a single carriage, the highly diagrammatic view of FIG. 2 will be used.

Figure 2:
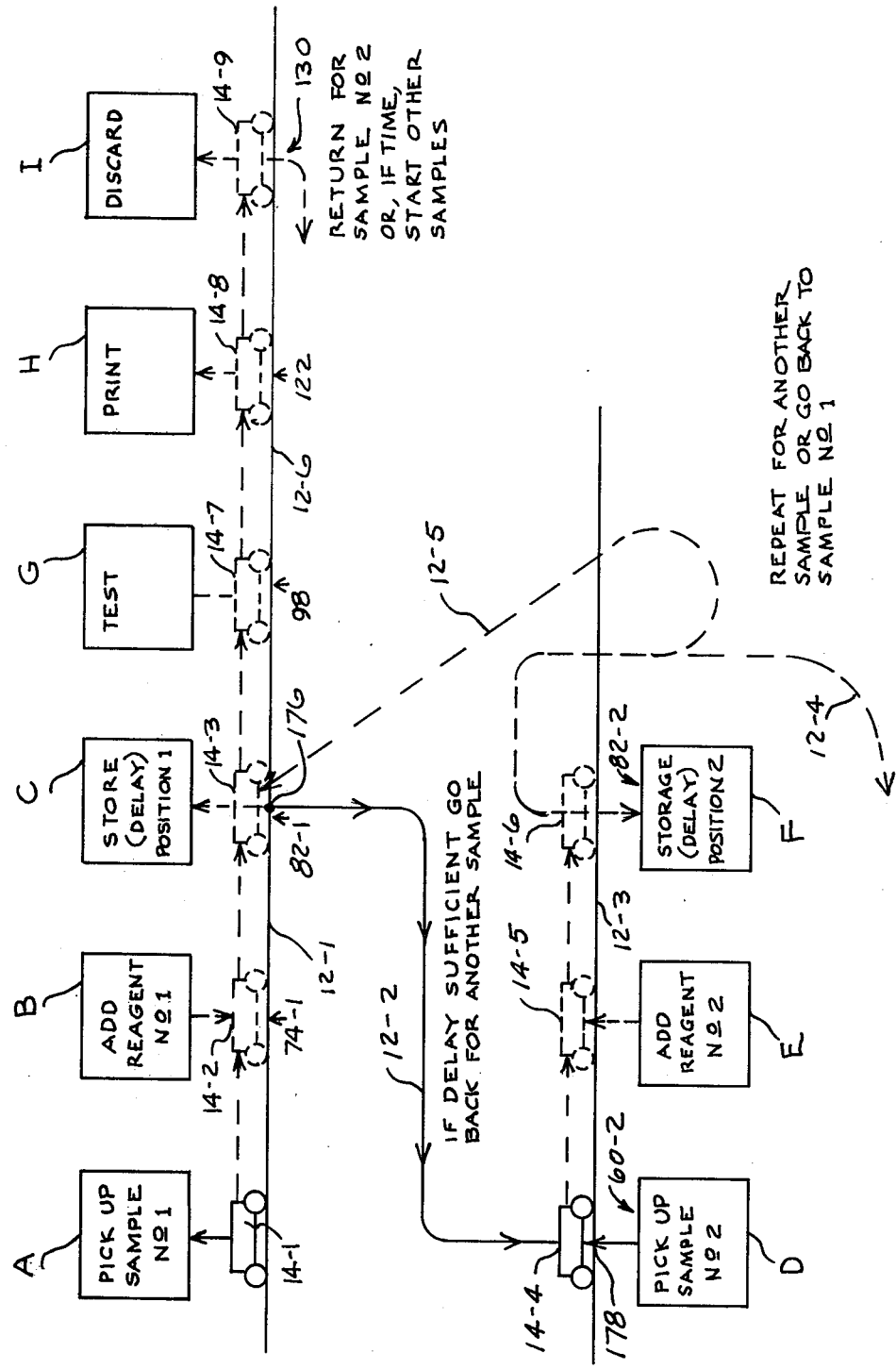
FIG. 2 is a highly simplified flow diagram demonstrating the manner in which two or more test procedures may overlap in time through the use of the invention.

FIG. 2 represents a simplified flow diagram of the operation of a single carriage device in performing the functions of an automated processing apparatus. The guideway 12 is here represented by the three lines 12-1, 12-2 and 12-3. It is emphasized that the display is graphical and not intended to signify that there are any branches or parallel extensions of the guideway. None of the channels or command circuitry is attempted to be represented in this figure.

Consider first that the carriage shown in solid lines at 14-1 picks up Sample No. 1 at station 60-1, this function being represented by the block A. The carriage now moves to station 74-1 where it is shown at 14-2 in phantom lines. Assume that at station 74-1 a quantity of reagent No. 1 is introduced into the sample container carried by the carriage, this function being represented by the block B. The carriage is now moved along the guideway 12-1 to the next zone where it stops at station 82-1, this being represented by the phantom lines 14-3. Here the testing procedure calls for, for example, the incubation of the sample at a certain temperature for a certain time, so the sample container is reciprocated from the carriage and inserted into a storage device. This function is represented by the block C.

At this point, designated 176, the apparatus has to make a decision. If the time of the delay at station 82-1 is not long enough to allow for the partial processing of another sample, the carriage waits at the point 176. If on the other hand there is sufficient time for other functions to be performed, the carriage leaves the point 176 and is sent to perform the other functions. Here it is assumed that the delay represented by the block C is more than enough for the carriage to be able to get another sample, insert another reagent and store the container in another location of the incubator or in another incubator. Thus, the carriage is returned by the program and control means giving the appropriate commands, such return being effected back along the same guideway. In order to show the return of the carriage, the guideway is offset and designated 12-2, this being the line commencing at point 176 and ending at the point 178. The carriage is shown at point 178 as a solid line member 14-4 and it is understood that it has returned back to the zone where it can pick up another sample container which is designated Sample No. 2. This is represented by the function block D. The location 60-2 is at the same zone as the location 60-1 but may be slightly displaced therefrom. If a carousel is involved, the locations 60-1 and 60-2 would be identical.

Assume that the carriage at 14-4 has picked up the second sample container containing the Sample No. 2 and is required to insert another reagent into the container. The carriage now moves forward (to the right in FIG. 2) along the same guideway, but now designated 12-3 to show the path actually being taken, to the reagent-adding zone. Here, at location 74-2 the carriage stops as shown by the phantom lines 14-5 and Reagent No. 2 is injected into the sample container as indicated by the function block E. The carriage now moves along the same guideway to the storage zone and stops at position 82-2 which must be different from the position 82-1 since there is already a sample container in a stall at this latter position. The carriage is designated 14-6 at this location and when the position is reached, the second sample container is inserted into the stall of the incubator at that position to be left there for a predetermined time.

From this position, the carriage has several ways that it may go, depending upon the amount of time which is available. If the samples No. 1 and No. 2 are going to be incubating for a considerable time, the carriage may go back to zone 60 and pick up a third sample. This is indicated by the broken line 12-4. If Sample No. 2 can be stored and Sample No. 1 is ready to be further processed, the carriage may move along the broken line 12-5 back to position 82-1 at point 176 and pick up the container of Sample No. 1 to finish processing it. This would move the carriage along the guideway as designated at 12-6 to the testing zone, the readout zone 122 and the discard zone 130 has shown at 14-7, 14-8 and 14-9, respectively. Here the functions to be performed would be test G, print or readout H and discard I.

Another possibility for the operation of the apparatus is for the carriage to complete the processing of the Sample No. 2 by-passing the stored Sample No. 1 because there is more time going to be required for the incubating of Sample No. 1 than there is in the incubating, testing, readout and discard of Sample No. 2.

From zone 130, the carriage will go back to perform other processing functions in accordance with instructions from the program and control means 134.

At this point, perhaps the timing involved should be considered. The apparatus described in connection with FIG. 2 has been given the two consecutive samples to process and the test procedure in each case may or may not be different. The apparatus is exhorted to process these samples in the shortest time to the end that the maximum amount of operating time can be obtained from the apparatus with the maximum throughput. Assuming that the carriage movement is instantaneous, the apparatus works out the carriage movement by suitable logic circuitry of a type that is well known as in the following examples. In these examples it may be taken that the times for processing are defined as $$T1 = TA + TB + TC + TG + TH + TI$$

and $$T2 = TD + TE + TF + TG + TH + TI.$$

The first expression is the processing time for Sample No. 1 and the second for Sample No. 2. Total time in each case is the time for picking up the sample at the sample supply zone and reading its test code (TA or TD) plus the time required to insert a quantity of reagent into the sample container (TB or TE) plus the time for which the sample is stored in the incubator (TC or TF) plus the testing time (TG), the readout time (TH) and the discard time (TI). In a practical machine, TA will equal TD; TB will usually equal TE; and TG may have different values for different tests. For purposes of explanation, we have assumed that there is only one test apparatus and that the time for testing is the same for all procedures.

EXAMPLE 1

If T2 is less than TC then from the point 176 of FIG. 2, the carriage can go back to the sample storage zone, pick up Sample No. 2, insert reagent, incubate, test, print and discard while Sample No. 1 remains in the incubator. When Sample 2 has been tested and its results recorded, the carriage can go back to the incubating zone, pick up sample No. 1 at the end of its incubating period and finish its test procedure.

In the above example, the savings in time with just the one additional processing of Sample No. 1 (and of course there could have been more than the one) is the complete processing time of Sample No. 2.

EXAMPLE 2

If [TD + TE + TF] is less than [TC + TG + TH + TI + TD] then Sample No. 1 must be processed before taking any of the test procedure steps with Sample No. 2 except picking it up from the sample supply means and reading its test code and returning it to the sample supply means.

In this example, if Sample No. 1 was to be left to incubate, Sample No. 2 picked up, supplied with reagent and placed in the incubator and then Sample No. 1 again picked out of the incubator and continued to be processed, it is necessary that the processing of Sample No. 1 through test, readout and discard to be completed before the incubation time of Sample No. 2 has been completed. If otherwise, the carriage would be in the middle of doing something which it could not interrupt when the Sample No. 2 has to be removed from the incubator and immediately tested. Of course there could be structure which would enable the Sample No. 1 to be held up before discard so that the carriage could go back for the critical processing of Sample No. 2, but the simplified form of the apparatus would not include this. The use of a second carriage would provide the flexibility needed to prevent this problem.

In other words, once Sample No. 2 has been placed in the incubator, the completion of Sample No. 1 must be effected before it is necessary to remove Sample No. 2 from the incubator.

What will happen is that once Sample No. 1 has been placed in the incubator, the carriage will be sent back to zone 60 and pick up the next sample. Since the samples are stored in the cassettes or on the carousel at random, there is no way of testing the formula of Example No. 2 without reading its test code. The apparatus may have a minimum time for testing built into its memory so that even for the fastest test procedure, there will be sufficient time for the carriage to leave one sample in the incubator and run back and see what the next sample requires. If there will not be sufficient time as described, after reading the test code and rejecting the concurrent testing procedure, the carriage will move to its position at the incubator and finish the test procedure it was working on.

EXAMPLE 3

If (TC + TG + TH + TI) is greater than (TD + TE + TF) Sample No. 1 can be stored; Sample No. 2 picked up, provided with reagent and stored; the carriage returned to Sample No. 1 picking it out of the incubator and finishing the test procedure thereof; the carriage returned to the incubator picking up Sample No. 2 and finishing the test procedure thereof.

There are many variations of the above examples, especially where more than two samples become involved. The circuitry for working out the logic is well known, as explained.

Depending upon the types of test involved, the procedures may permit interruption for purposes of recommencing another procedure which has been delayed. All of this type of logic can readily be worked out and built into the program and control means 134.

Figure 3:
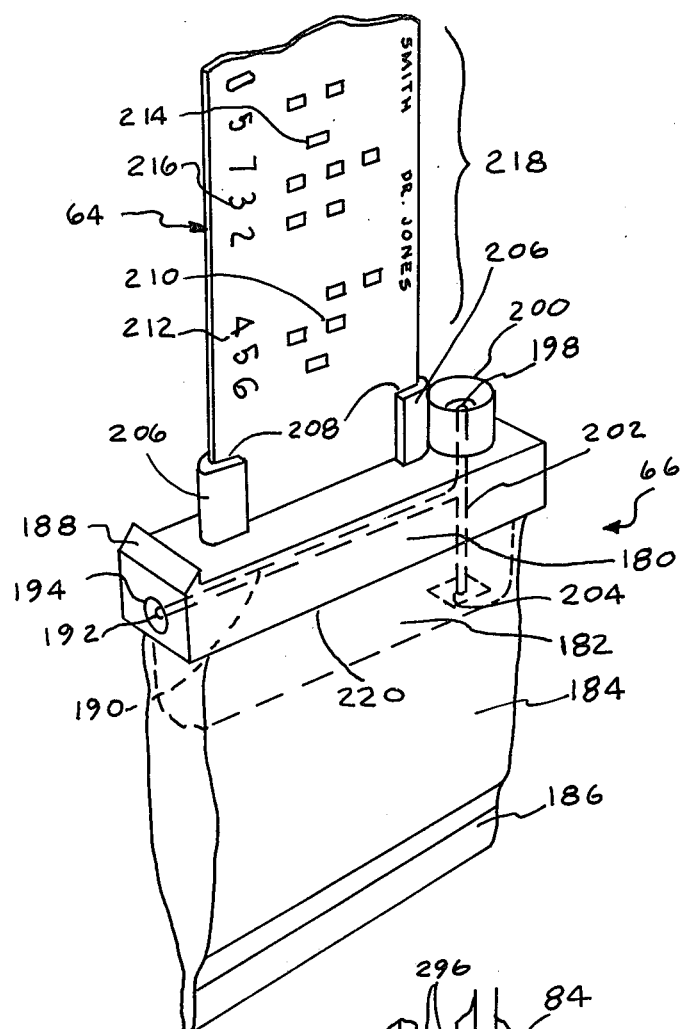
FIG. 3 is a perspective view of a sample container and indicia means embodying the invention of U.S. Pat. No. 3,647,386 with slight modification, suitable for use with the invention herein.
Figure 4:
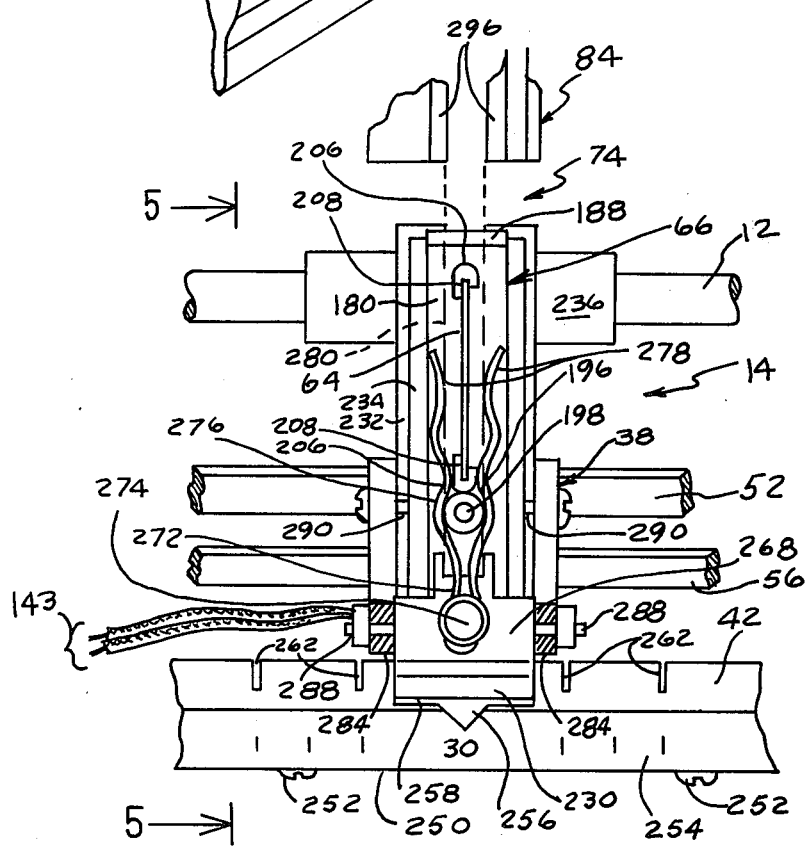
FIG. 4 is a top plan view showing a sample container mounted on a carriage of the apparatus of the invention, a portion of the environment of the carriage being fragmentarily shown.
Figure 5:
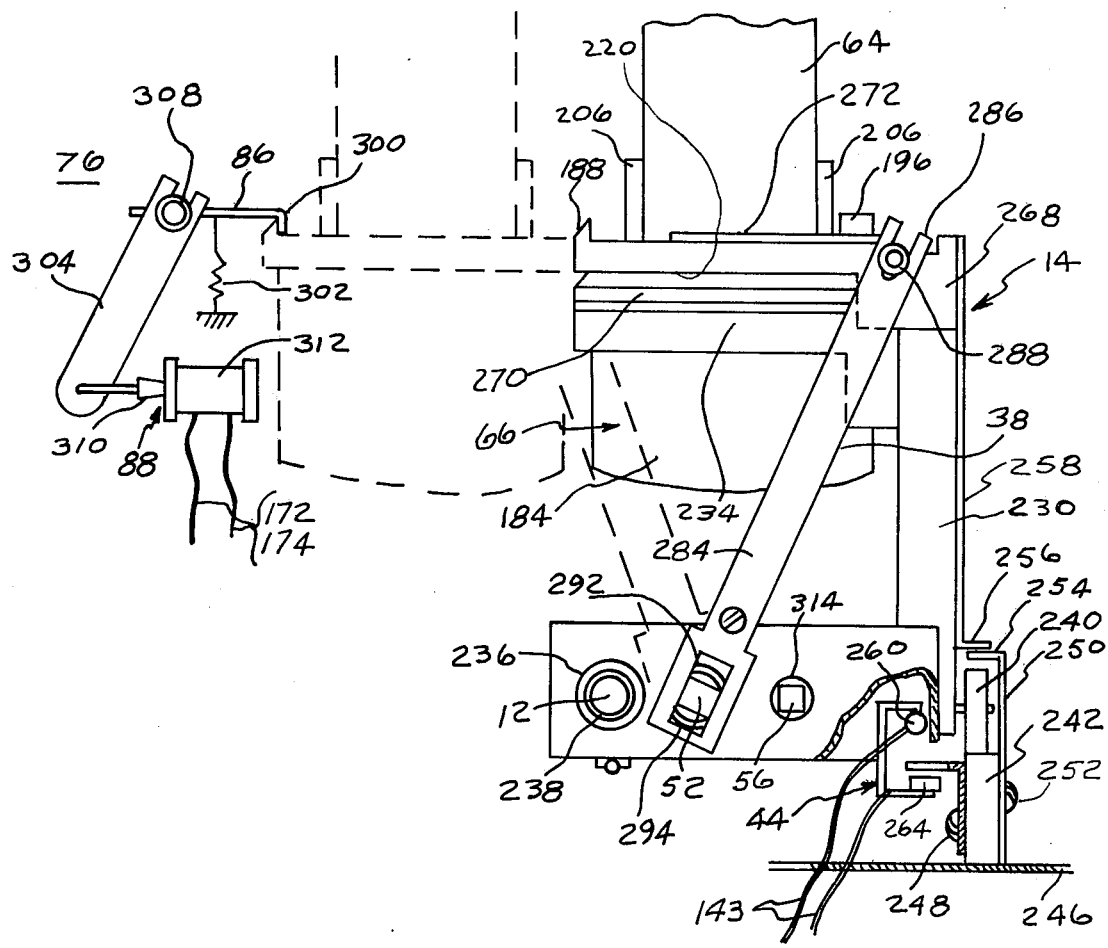
FIG. 5 is a side elevational view taken generally from the plane identified as 5—5 in FIg. 4 and in the direction indicated.

Reference may now be had to FIGS. 3, 4 and 5 which illustrates some of the details of examples of the first embodiment of sample container 66 and the carriage 14 by reason of which the apparatus 10 may be better understood. It should be emphasized that these structures are capable of wide variation and the basic concept is intended to be convered in the appended claims without limitations represented by the details.

The sample container 66 of FIG. 3 is constructed in accordance with the disclosure of U.S. Pat. No. 3,647,386 with some variations. There is an elongate body member 180 of rigid plastic having a generally square cross section but having a somewhat smaller depending extension 182 upon which there is sealed or cemented a soft plastic bag the bottom of which is also sealed as indicated at 186. This structure permits of mixing the contents by kneading or otherwise working the bag 184, and, although not specifically described in connection with the apparatus 10, means normally would be provided to assure that the contents of the bag 184 are thoroughly mixed after the addition of the reagents at zone 74.

The left-hand end of the body member 180 has an upwardly extending tooth 188 integral therewith, this tooth 188 being intended to cooperate with the latching bar 86 when the container 66 is stored in a stall of the container storage apparatus 84. There is an elongate passageway 190 in the head 180, the entrance to which can be seen at the left at 192 in a cuplike conical depression 194 which enables a reagent nozzle such as 78-1, 78-2 and 78-3 to pilot and seat during the introduction of reagent into the container 66. At the top of the head 180, opposite the lefthand end in FIG. 3 there is a cylindrical post 196 having a central opening 198 in a depression 200 similar to 194 leading to a vertical passageway 202 that intersects with the passageway 190 but continues downward to the bottom of depending extension 182 and opens into the bag 184 past a flapper valve 204. There will be some arrangement at the junction so that when reagents are forced into the passageway 190 they will pass into the vertical passageway 202 downwardly and into the bag instead of emerging upwardly from the opening 198. Examples of this type of structure are described in the above-mentioned patents of the assignee. It should also be pointed out that these patents also describe an arrangement by virtue of which the undiluted fluid which is to be tested is initially contained in a short length of capillary tubing that is inserted and carried in the passageway 190. The first dilution of the fluid is achieved by forcing a volume of the diluent into the passageway 190 and through the bore of the capillary tubing thus washing all of the undiluted fluid out of the length of tubing and into the bag 184. This initial dilution could be done in the apparatus 10 or prior to installing the container 66 in the cassettes such as 68.

The openings and passageways which have been described in connection with FIG. 3 comprise the access means which are referred to herein. It should be appreciated that one, two or more openings could provide the means for introducing liquids and reagents into the bag 184 and for removing the same therefrom.

On the upper surface of the head 180 there is provided a pair of integral upwardly arranged guide members 206 each having an internal vertical groove 208 thereby providing a seat between them for the insertion of a removable rectangular identification card 64 previously referred to as indicia means. The card can carry any desired information, but preferably it will carry a printed or punched machine-readable code 210 identifying the test procedure to be followed, this same code in human readable indicia at 212, a sample identification at 214 which is machine readable at 216. Other human readable information may be shown at 218 giving patient and doctor's names, etc. The card 64 is readily installed and removed from the seat provided by the grooves 208.

The head 180 is constructed in such a manner that lateral shoulders 220 are provided along its lower edges between the outer lateral sides and the extension 182. The thickness of the upper mouth of the bag 184 which is engaged on the extension 182 is minimal so as not to interfere with the use of the shoulders 220 for supporting the bag on the carriage as will be explained and sliding the bag onto and off of the carriage in moving the same.

The carriage 14 with a sample container 66 disposed thereon is shown in its operative arrangement in FIGS. 4 and 5. The first of these is a generally top plan view of a fragment of the apparatus 10 which includes the carriage, and the second of these is a fragmentary view generally taken along the plane 5—5 of FIG. 4. The carriage 14 is generally capable of substantial variation in construction; hence the details which are given are intended only by way of example. There is a vertical standard 230 having a bottom block member 232 connected therewith that extends to the left as viewed in FIG. 5 and a similarly arranged upper block member 234. This structure is generally of C-shaped configuration and its opening faces the various zones 60, 74 and 82 in FIG. 1 providing a generally convenient arrangement for the reciprocation of the sample container onto the upper block member 234 without interference.

The carriage 14, as explained, is intended to be slid along the guideway 12 right and left as viewed in FIG. 1, and for this purpose the left-hand end (rear) of the lower block member 232 has a passageway formed at the axis of an integral cylindrical housing 236 which carries an antifriction sleeve or bearing 238 through which the guideway 12 is engaged. In this example of the apparatus 10, the guideway 12 is a cylindrical rod of smooth metal. The carriage 14 and housing 236 are of plastic, such as a molded rigid synthetic resin. The front (right-hand end in FIG. 5) of the carriage 14 is provided with a free-rolling roller 240 that engages a track 242 mounted to the support or framework 246 of the apparatus 10.

The scale 42 which has previously been mentioned has an angled portion by means of which the scale is fastened to the lateral face of the track member 242 by any suitable means such as the screws 248. A metal shroud 250 is also secured to the track member 242 along the front thereof by screws 252, this shroud being substantially coextensive with the scale 42 and concealing the same as well as protecting the track and the roller 240. The upper lip 254 may have the same divisions marked off as the divisions of the scale 42 cooperating with a pointer 256 carried by a bracket member 258 on the standard 230 whereby to identify exactly the numerical location of the carriage 14 along the scale 42.

For identifying the exact location of the carriage 14 at all times, the carriage has a structure 44 previously mentioned which cooperates with the segments of the scale to count them off and store the information in the memory of the program and control means 134. This structure includes a mounting member having a lamp or other light source 260 which projects a beam of light downward onto the top of the scale 42 and through the slits 262 of the scale 42 onto a photoresponsive device 264 as the carriage moves. The number of slits passed in moving relative to the zero reference points 48 or 50 gives information on position.

The carriage 14 has a reciprocating device 38 for picking up and discharging sample containers in the manner explained. The reciprocating device includes a crosshead 268 having inwardly directed flanges (not shown) that are engaged in opposite grooves 270 provided in the upper block member 234 by means of which the crosshead 268 is enabled to slide frontward and rearward when so moved. This movement is normal to the guideway 12. The top of the crosshead 268 is provided with a rearwardly extending resilient wire clip 272 of generally hairpin configuration, the bight being held in place by a screw and washer fastener structure 274 and there being an intermediate gripping structure 276 formed by suitable arcuate facing bends formed in the arms of the clip 272. The arms extend substantially rearward as indicated at 278 and are bent to bear downward. The upper block member 234 has a large slot 280 along its length, and when the carriage is moved rearward in a manner which will be described and a sample container is picked up by the reciprocating device 38, it can be pulled forward onto the carriage 14. The shoulders 220 will ride onto the top of the block member 234 and the bag and depending extension 182 will freely be accommodated in the slot 280.

In picking up a sample container, the crosshead 268 is moved rearward and the arms 278 engage on the top of the block 180 of the sample container 66 which, for example, is carried in a cassette 68. Assuming that the sample container is supported in the cassette 68 by its shoulders 220, it can be seen that there is no interference with the structure of the cassette 68. The arms 278 of the clip 272 straddle the post 196 and pass on opposite sides of the guide member 206, the clip 272 moving forward with the crosshead 268 until the post 196 is forced into the tight gripping seating structure 276 which tightly grips the post 196. Thereafter, if the crosshead is returned forward onto the carriage 14, it pulls the sample container 66 with it and onto the top of the upper block member 234 where the bag 184 hangs freely in the slot 280.

To effect movement of the crosshead 268 there is provided a pair of swinging arms 284 the upper ends of which are forked at 286 and engage pins 288 mounted to the crosshead 268 and protruding from opposite sides. Washers are shown holding the forked ends 286 in place. The arms are connected together by the cross shaft 290 that passes across the opening of the C-shaped configuration forming the carriage 14, and the bottom ends of the arms 284 have rectangular seats 292 into which the square shaft 52 is engaged. A bearing 294 with a square bore is mounted in the bottom block member 232 and the shaft 52 also passes through this bore thereby providing an antifriction mounting for the shaft in the carriage 14.

The swinging movement of the arms 284 occurs about the axis of the bearing 294. When the arms are in the solid line condition of FIG. 5 the sample container 66 is on the carriage 14. To move it off the carriage the arms are rotated in a counterclockwise direction to the broken line position in FIG. 5.

Suitable structure is provided for supporting, retaining and releasing the sample containers during the operation of the apparatus 10. For example, in connection with the incubator or storage device 84 it is required that the carriage 14 install and remove sample containers. For this purpose, the stalls or positions of the apparatus 84 can be provided with grooves or slots having ledges such as shown at 296 to support the shoulders 220 of the body 180 when the sample container 66 is inserted. To retain the sample container 66 in a given stall and to pull it off the carriage, there is a latch bar 86, and to release it there is a latching mechanism 88. The latch bar 86 has a forward lip 300 normally pulled downwardly by the spring 302 to cause rotation of the lever 304 in a clockwise direction around the pivot 308 pulling the armature 310 of the solenoid 312 to the left in FIG. 5. When the body 180 is pushed into a stall, the tooth 188 rides against the lip 300 and lifts it together with the bar 86, passing under it. Then when the body 180 is pulled forward by the crosshead 268, the lip 300 hooks into the tooth 188 and resists the forward movement. The post 196 of the sample container 66 is pulled out of the structure 276 of the clip 272, leaving the sample container in the storage device 76.

When it is desired to retrieve the sample container, again the crosshead moves rearward and the clip 272 engages with the post 196. At this time, an appropriate signal from the program and control means 134 energizes the solenoid 312 on lines 172 or 174, pulling the armature 310 to the right in FIG. 5 and rotating the lever 304 counterclockwise. The latching bar 86 is fixed to the lever 304 and hence the lip 300 is raised and the following forward movement of the crosshead 268 carries the sample container 66 out of the stall and onto the carriage 14 where it remains.

The carriage 16 operates in the same manner as explained for the carriage 14 except that the location of the crosshead moving arms equivalent to the arms 284 is slightly different on account of the use of the shaft 56 instead of the shaft 52 for moving the crosshead of the carriage 16. Note that the shaft 56 passes freely through a round hole 314 in the lower block member 232. There is an equivalent hole in the lower block member of the carriage 16 to accommodate the free rotation of the shaft 52.

As explained above, the system of the invention herein is especially intended for use with a method of feeding samples to the apparatus 10 that involves acquiring the initial biological fluid in the form of a precise volume that is contained in a short known length of capillary tubing. U.S. Pat. Nos. 3,475,127, 3,647,386 and 3,645,252 are concerned with this technique. On this account the specification above describes the cassette 68 as containing a plurality of containers 66 of the construction illustrated in FIG. 3. Each such container has its individual length of capillary tubing containing the blood or blood serum or other basic fluid which is to be diluted with some reagent to make the desired mixture to be tested. This would presume that each of the containers in a cassette such as 68 is inserted into position within the cassette with its own length of capillary tubing in place and that the testing proceeds as described hereinabove.

The invention is not limited to this method of automatic testing. In the case of some known systems, the fluid which is to undergo plural tests is divided into aliquots by the apparatus itself. Thus, the fluid such as blood or serum or the like is disposed within a single sump or holder from which it is doled out in small amounts to a plurality of reaction vessels. The reaction vessels are then diluted, respectively, with the reagents that are to provide the mixture to be tested. The invention is capable of being carried out in this same manner insofar as deriving the containers with individual aliquots of sample. Once this has been accomplished, it is immaterial to the remainder of the apparatus 10 how such samples came about to be disposed in the respective containers. And the modifications necessary to accomplish this are relatively minor as will be pointed out, albeit novel in their way of accomplishing in a simple manner the division of a large volume of sample into a plurality of small aliquots. Importantly, the containers 66 or modified forms thereof can be used and hence may be discarded after testing has been effected.

Basically, as explained in connection with FIG. 6, the original sample of fluid which can be blood, serum or any other type of fluid which is to be tested by the apparatus 10, is contained in a single container. This container is associated with a plurality of empty containers, preferably in a single carrying structure such as for example, a cassette. To the apparatus which has already been described in detail, there is added a sample dispenser which is capable of withdrawing fluid from one container and dispensing the fluid in accordance with a volumetric control into another container. In the apparatus 10' of FIG. 6, all of the fluid is withdrawn from the single container and then each of the empty containers is filled with an aliquot by the dispenser. In this way, the need for filling the lengths of capillary tubing is eliminated together with the need for cutting the lengths into smaller lengths and inserting each individual length into a passageway such as 190.

Figure 6:
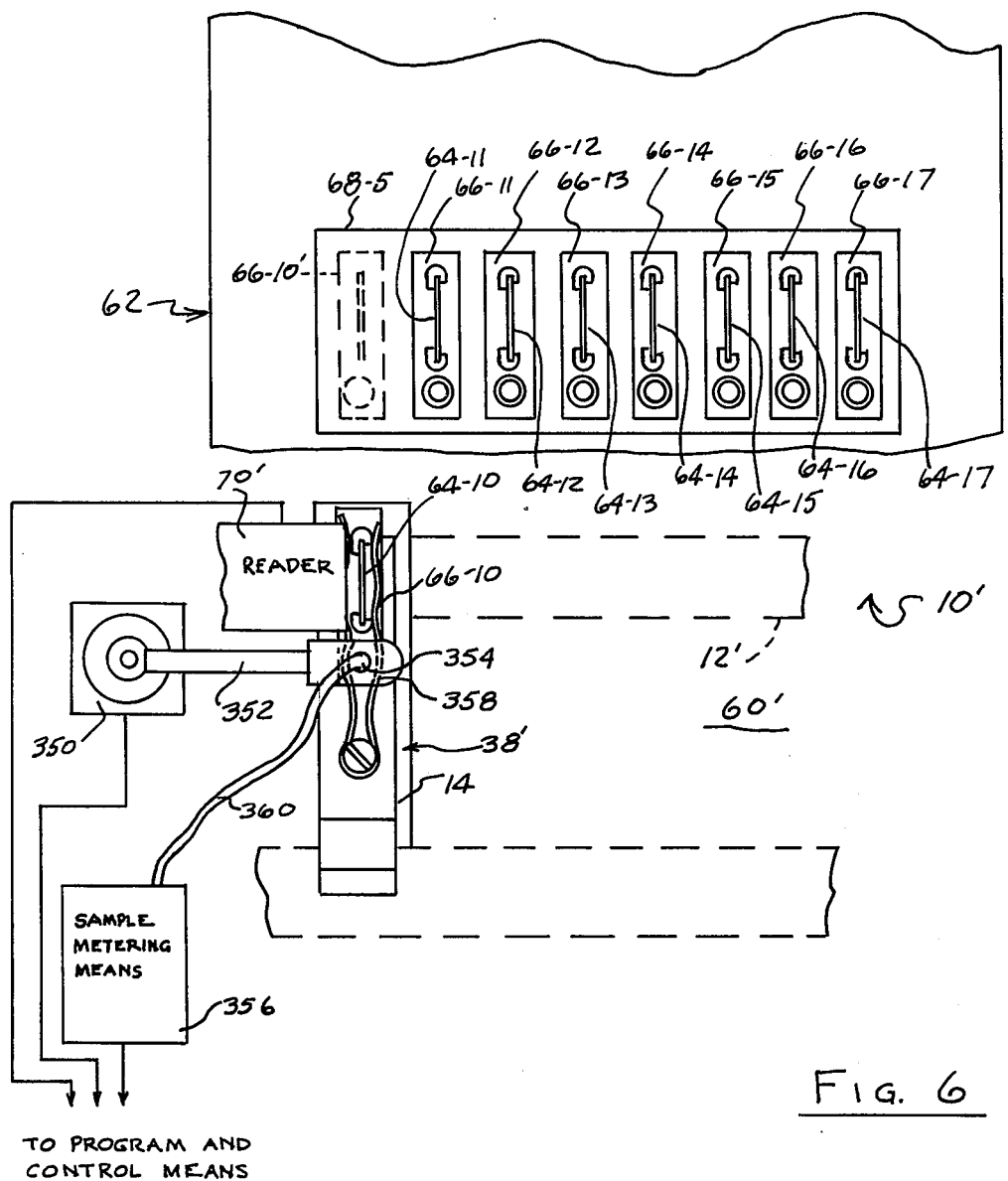
FIG. 6 is a diagrammatic view of a portion of a modified apparatus constructed in accordance with the invention, the view in particular illustrating modified sample container supply means.

As for the details, in FIG. 6, the sample supply means 62 has a cassette 68-5 which previously has been prepared by technician gathering the fluid to be tested, such cassette 68-5 having therein a container 66-10 which is shown in broken lines 66-10' to indicate that it was so located but has been moved. In FIG. 6 for purposes of explanation, the principal container 66-10 has been pulled out of the cassette by the mechanism 38' which can be the same as the mechanism 38 or 40 onto the carriage 14' which is similar to the carriage 14. The guideway 12', scale 42' etc. are the equivalent of the guideway 12, scale 42 and other apparatus described previously. The indicia means 64-10 of the container 66-10 will come into association with a reader 70' that can read the information container thereon. The same cassette 68-5 also has a plurality of other containers therein, shown at 66-11, 66-12, 66-13, 66-14, 66-15, 66-16 and 66-17 each having its own indicia means like the cards or members 64 previously described.

The difference between the arrangement of FIG. 6 and that previously described in connection with the apparatus 10 is that in the case of the apparatus 10' the cassette 68-5 carries only one container 66-10 with sample fluid when prepared originally. All of the other containers 66-11 to 66-17 are empty, but each is expected to be used in a different test and hence the indicia means of each is different from all others. Thus, there are as many different indicia means 64 as containers and these are designated 64-11 to 64-17 respectively.

The additional pieces of equipment which are associated with apparatus 10' that are not found in apparatus 10 are the vertically reciprocable snorkel moving means 350 which could be solenoid or air-cylinder operated, the arm 352 which extends over the carriage 14' at the initial indicia reading zone 60 carrying the snorkel 354 (only the top of which is seen in FIG. 6) and the sample metering means 356. The requirements for these articles of equipment are obvious from the general discussion of FIG. 6 but can be pointed out. The snorkel moving means 350 is required to be able to raise the end 358 of the arm 252 high enough so that it clears the carriage 14' and the container which is upon the carriage 14'. It must thereafter be capable of being lowered so that the bottom end (not shown) of the snorkel 354 will enter into the access means of the container on the carriage 14' at that time and pass into the bag equivalent to 184 and dip into the fluid which may be carried therein. Obviously, it has to align with the access means, which is the equivalent of the parts 196, 198 and 200 previously discussed. Each of the containers 66-10 to 66-17 will have such a post, opening, etc.

The connecting conduit 360 must be flexible to afford the vertically reciprocatory movement of the snorkel 354. The sample metering means must be in the form of a pump with a storage sump. Initially, it is required to withdraw from the sample container 66-10 sufficient of the sample liquid to be able to dispense an aliquot for each of the remaining initially empty containers. It must therefore have a mechanism to permit the metering of the fluid. Advantageously it will have a rinse mechanism which, for example, could be a similar or other container that carries wash liquid and indicia means that identifies a wash cycle which the reader 70' recognizes and advises the program and control means so that the wash cycle can be effected within the sample metering means before the next sample comes along.

The procedure which would be followed in using the apparatus 10' differs only in a minor way from the procedure for the apparatus 10. When the apparatus is started, assuming that the cassette 68-5 is in the position shown, the carriage 14' is located adjacent the reader 70'. The mechanism 35 has previously been raised so that the snorkel bottom is substantially above any possible interference with the carriage 14' or a container which might be brought into position on the carriage. The reciprocating mechanism 38' of the carriage 14' moves forward, seizes the container 66-10 and pulls it back onto the carriage. The reader 70' reads the card 64-10 and passes the information into the program and control means. Among this information is the information that this is a container which contains a large quantity of sample fluid which is to be tested in plural tests.

The mechanism 350 now responds to command signals from the programming and control means and lowers the snorkel into the container 66-10. When the bottom of the stroke is reached, the sample metering means 356 sucks the fluid out of the container and stores the same in a suitable sump within itself. The snorkel 354 is now raised, the container 66-10 pushed back into its stall in the cassette 68-5 or it could be quickly transported on the guide 12' to a discard mechanism like 133 of FIG. 1. The invention includes the possibility of bringing the container 66-10 back to the position shown in FIG. 6 to extract more sample therefrom. As a matter of fact, the sample metering means could conceivably be constructed to withdraw and dispense one aliquot at a time in which case the container 66-10 would be withdrawn and returned the same number of times that there are empty containers in the cassette 68-5, in this case seven times. Preferably, in the interest of maximum throughput, the sample metering means should be able to do all of the dispensing without being required to call upon the first container 66-10 for additional sample.

Assuming that the sample metering means 356 has now drawn all of the fluid from the container 66-10 and that the latter container is back in its stall or otherwise out of the way, the carriage 14' is moved to the right to the second stall of the cassette 68-5 (or in the alternate, the cassette itself could have been moved to the left). The pickup mechanism 38' moves into the stall, picks up the container 66-11 which, as explained previously, is empty, and when the container is in position on the carriage 14' moves to the left until the reader 70' is adjacent the indicia means 64-11. The test information contained on that indicia means 66-11 is read and stored. The snorkel 354 is now lowered into the container bag and the sample metering means 356 dispenses an aliquot of the sample fluid into the container 66-11. The snorkel 354 is raised out of the container 66-11 and the carriage 14' moves to the right to start the procedure of injecting reagent, storing, etc. that was explained in connection with the apparatus 10. Thus, from the point of time that the container 66-10 has its aliquot of sample fluid onward, it is treated no differently than the containers that are being processed in apparatus 10 after their test code has been read by the reader 70.

Assuming that the carriage 14' is free of the container 66-11 by virtue of having stored it in the container storage 84 or completed its test or having passed it on to another carriage similar to the carriage 16, the carriage 14' returns for another container to the zone 60'. It moves directly to the third stall of the cassette 68-5, stops there, picks up container 66-12 which is empty, then moves to the reading position alongside of the reader 70'. The test code is read from the indicia means 64-12, the snorkel 354 lowered, an aliquot of the sample pumped into the container 66-12, the snorkel raised, and the container 66-12 is now started on the procedure which has been called for by its code. The test will normally be different from that of the first since it is to be expected that the technician will put only a single sample of fluid in a cassette along with the number of empty containers corresponding to the number of different tests to be made on that one sample. It is clear that there will be a different card or slip (indicia means 64-11 to 64-17) for each test and that the order of the tests can be a random one.

But for the time required to position the first container, withdraw the sample fluid therefrom and return it, the only time lost in a practical device will be the movement of the carriage from a stall of the cassette to the reading position. The reader 70 would preferably be fixed because the snorkel location is also preferably fixed. Otherwise, there is no appreciable loss of time when comparing the operation of the apparatus 10' with that of the apparatus 10.

Figure 7:
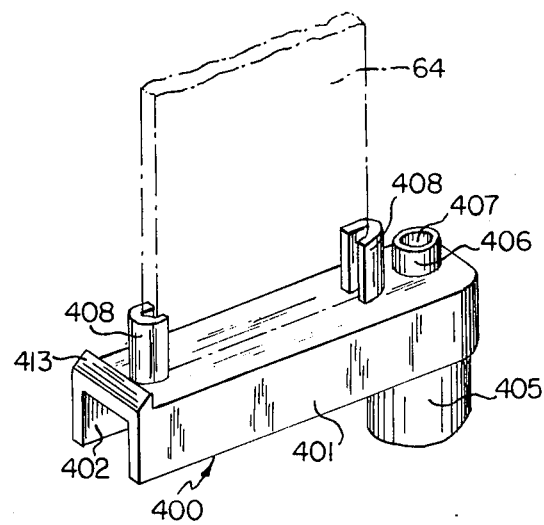
FIG. 7 is a perspective view of a second embodiment of sample container for use with the invention herein; and, FIG. 8 is a side elevational view similar to FIG. 5 but showing the second embodiment of sample container of FIG. 7 in its environmental use with the invention herein.
Figure 8:
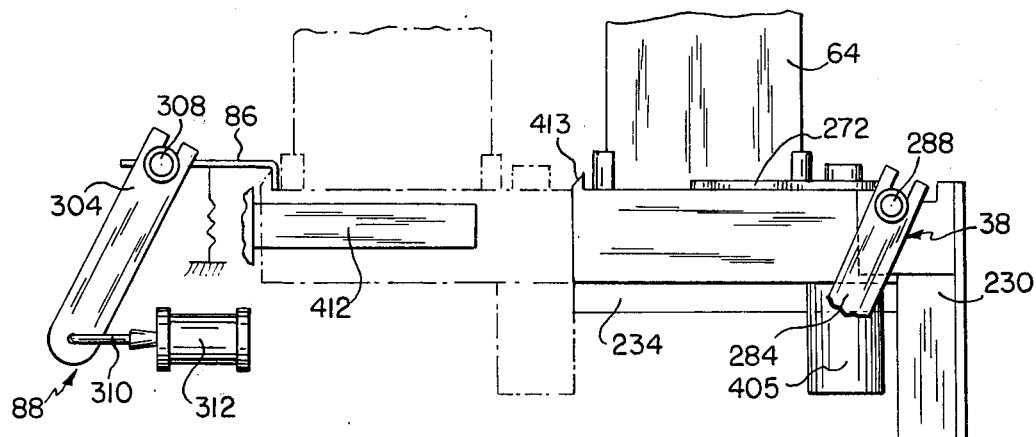

In FIGS. 7 and 8 a second embodiment of sample container 400 is shown which includes a rigid generally inverted U-shaped rectangular body 401 thus defining a channel 402 extending centrally therethrough.

An elongated cylindrical container 405, also preferably formed of rigid plastic material, is suitably affixed to the underside surface of the body 401 adjacent its trailing end thereof. The container 405 is intended to hold a suitable quantity of fluid to be analyzed, and although not herein shown, a flea, as sometimes referred to in the art, or a minute agitator as also called, may be disposed in said container, being freely movable therein as resulting from the movement of the container 400 throughout its test procedure to provide and sustain suitable mixing of the said fluid.

As best seen in FIG. 7, an upstanding cylindrical post 406 is provided with port 407 extending therethrough to communicate with the chamber of container 405 whereby to permit access thereto for the same purposes as hereinbefore enumerated with respect to the port 198 in sample container 66.

The container body 401 is also provided with a pair of upstanding guide members 408 on the top surface and which are intended to hold the indicia card 64, as in the previous embodiment of container 66.

The present configuration of container body 401 is also adapted to be reciprocally moved by the reciprocating device 38 to and fro of each of the plurality of stations along guideway 12.

For this purpose, and with the container 400 disposed in the reciprocating device 38 as seen in the solid line position therefor in FIG. 8, the container body 401 rests upon the block member 234 in the same manner as in the previous embodiment of container 66.

The retaining clip 272 releasably holds the container body 401 on the block member by frictionally engaging the cylindrical post 406, and adjacent guide member 408.

When it is desired to discharge the container 400 from the reciprocating device 38, said device is actuated as is previously described to swing arms 284 to the left as seen in FIG. 8 effective to slide the container 400 also to the left as viewed toward the intended station depository.

As seen in FIG. 8, an elongated rail 412 is located at each station and positioned to enter into the container channel 402 as the container is moved toward said intended station.

The rail 412 is positioned so as to locate the container in its proper test position at each station and is constructed as to permit the container to freely slide thereover.

When the container 400 is moved to its test position at the intended station, the latch drive mechanism 88 is intended to retain the container in place while the reciprocating device 38 retracts preparatory to its being programmed to another container pick-up location.

For this purpose, the container body 401 is provided on its leading end with an inclined tooth 413 that is adapted to lift or pivot the latch bar 86 about its pivot 308 as said container is being moved to the left as viewed in FIG. 8 toward its test position whereat the forward lip 300 of said latch bar rides over and drops down behind said tooth to releasably lock the container 400 in its test position at the selected station as is shown in dotted lines in FIG. 8.

The reciprocating device 38 may then be actuated to move or retract its block member 234 toward the right as viewed in FIG. 8 whereupon the container 400 is pulled free of the retaining clip 272 thereby leaving the container 400 at its test position at said selected station.

At the conclusion of the selected test procedure, the reciprocating device 38 may be again actuated to the left as viewed in FIG. 8 whereupon the clip 272 releasably grasps the container 400. The solenoid 312 is then actuated to lift the latch bar 86 about its pivot 308, and the reciprocating device 38 is retracted to the right as viewed in FIG. 8 to slide over the rail 412 and out of the test station position preparatory to its being moved along the guideway 12 to the next test station as indicated in its test procedure.

Figure 9:
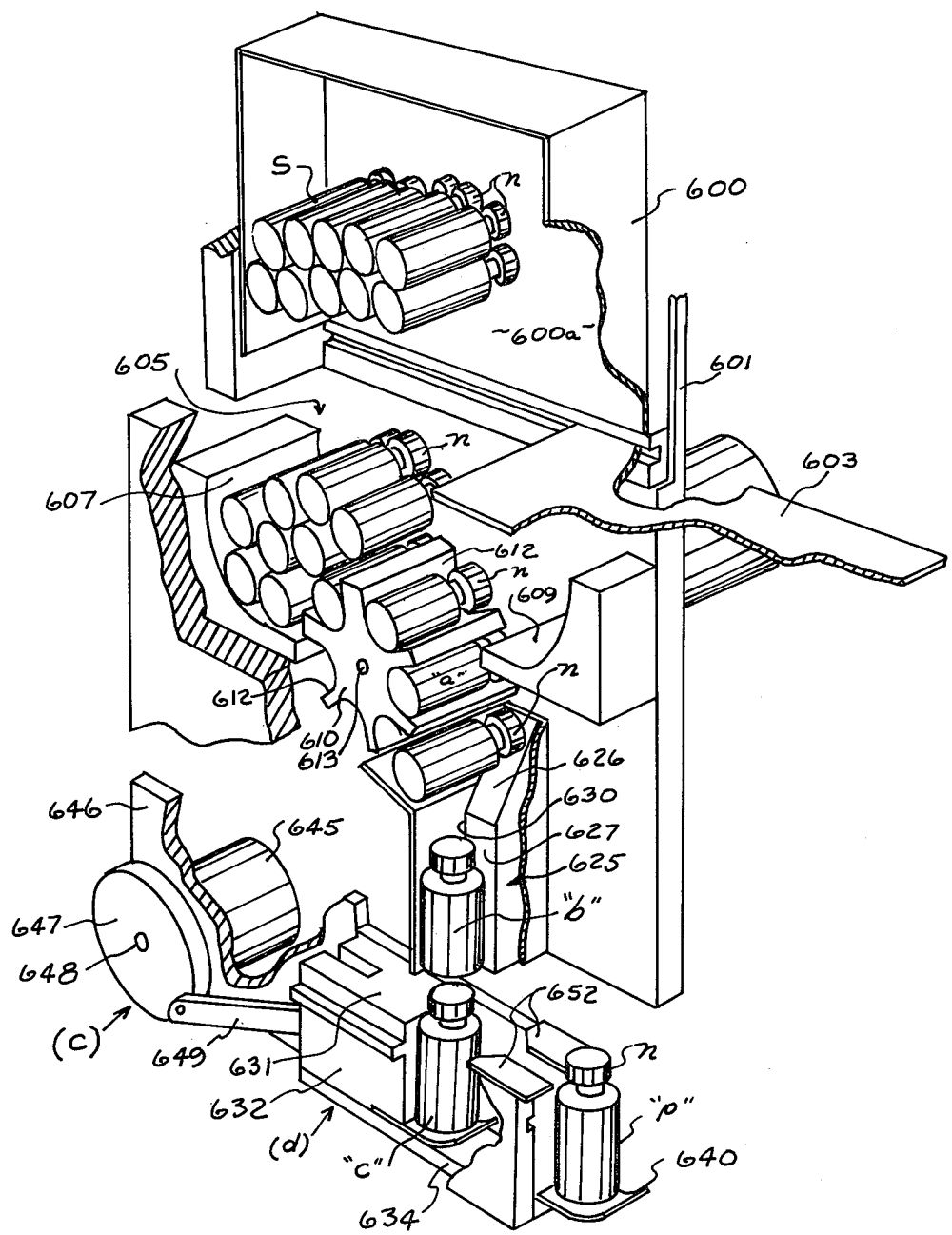
In FIGS. 9–12 is another embodiment of apparatus incorporating the features of the present invention.
Figure 10:
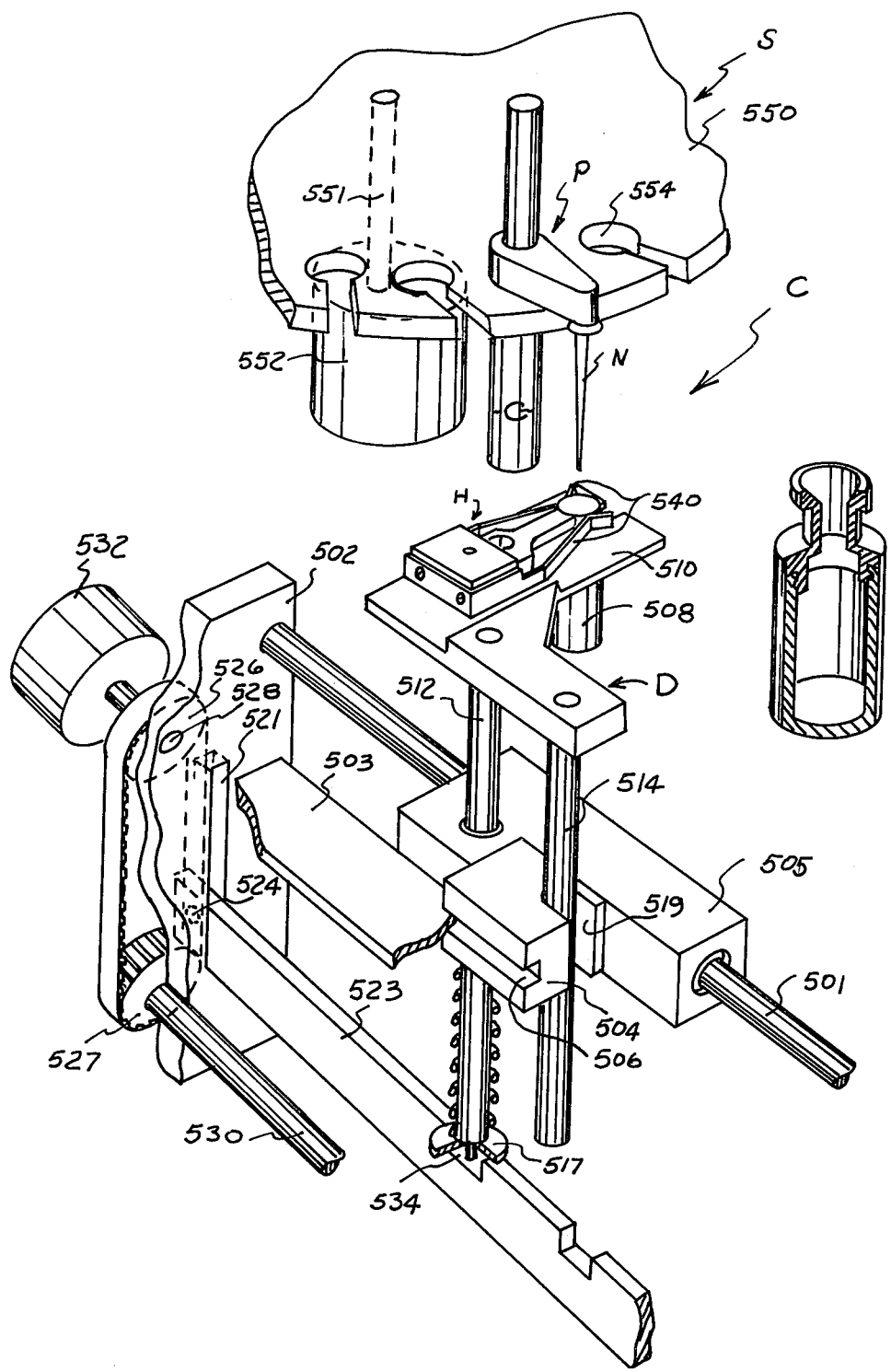

Referring to FIGS. 9–12 where is illustrated another embodiment of apparatus incorporating the inventive features herein, in FIG. 10 is disclosed a sample supply, dispensing and carriage mechanism as is identified generally at C. This mechanism includes a carriage D which is movable along the guideway 12' comparable to guideway 12 of the initial embodiment, and which, in its alternate form includes a rod 501 extending longitudinally along the processing path of the apparatus, and which, as shown, is attached at its ends (only one of which is shown) to an upstanding plate 502 located at each end of said path.

A flat rail 503 attached at its ends to the upstanding plates 502, extends along said processing path. Block member 504 attached to the rear side of the base member 505 of the carriage is formed with an elongate slot 506 which slidably embraces the rail 503 as to provide additional support and guidance therefor.

A serum cup or container 508 is shown being releasably held at its neck by the cup holder H of the carriage D being thereby movable by said carriage along the processing path to the sample fluid dispensing station S. Only one carriage D is shown in FIG. 10; however, it is intended to have at least two such carriages comparable to carriages Nos. 1 and 2 of the initially disclosed embodiment of FIGS. 1 and 4, and which are comparably operable to perform their respective work functions as are disclosed herein.

The cup holder H includes a platform 510 mounted in the upper ends of a pair of post members 512 and 514. Post member 512 projects downwardly from the underside of platform 510 and projects freely through hole 515 formed in the carriage base member 505. The free end of post member 512 carries a disk-like element 517, and a coil spring 518 is placed over said post member being disposed between element 517 and the underside of the base member 505, and thus operable to urge the base member downwardly as viewed in FIG. 10.

Post member 514 also projects downwardly, as viewed in FIG. 10, from the underside of platform 510 and freely extends through a slot 519 formed in the end wall of block member 504.

With this construction, the carriage D is intended to be raised upwardly at the sample fluid dispensing station S from its FIG. 10 position to an elevated fluid dispensing position whereat the nozzle or tube N of the sample fluid dispensing apparatus is disposed within the serum cup 508 preparatory to depositing therein a sample of a patient's fluid to be tested.

To accomplish the raising of the carriage D, the end plates 502 (only one being shown in FIG. 10) are each formed with an elongated vertically extending slot 521.

A bar member 523 has its ends disposed within said slot 521 as to be freely slidable therein, and each end is securely fastened at 524 to an endless belt 525 carried about gear wheels 526 and 527. Gear wheel 526 is rotatably mounted in stub shaft 528 carried on the end plate 502, and gear wheel 527 is similarly mounted on the end of drive shaft 530 rotatably suspended between the said end plates 502. A suitable motor 532 is drivingly connected to shaft 530 and is intended to be actuatable to rotatably drive said shaft and endless belt 525 between its FIG. 10 position, counterclockwise sufficiently to raise the bar member 523 upwardly within slot 521. The bar member 523 is disposed directly underneath post member 512 and is further provided with a plurality of spaced upwardly facing slots 534 into one of which the disk-like member 517 on the end of post member 512 is intended to be located to thereby releasably retain the carriage D in the position shown in FIG. 10 at the sample fluid dispensing station S.

Such construction thus enables the bar member 523 to be elevated by motor 532 and endless belt 525 and raise the carriage D upwardly and to position the dispensing nozzle or tube N in the serum cup 508 then being held in holder H.

As shown in FIG. 10, the serum cup holder H includes a pair of resilient fingers 540 configured to releasably grasp a serum cup 508 at its neck portion so as to properly position the same to receive a fluid sample of a preselected patient from the aforesaid nozzle or tube N.

Figure 11:
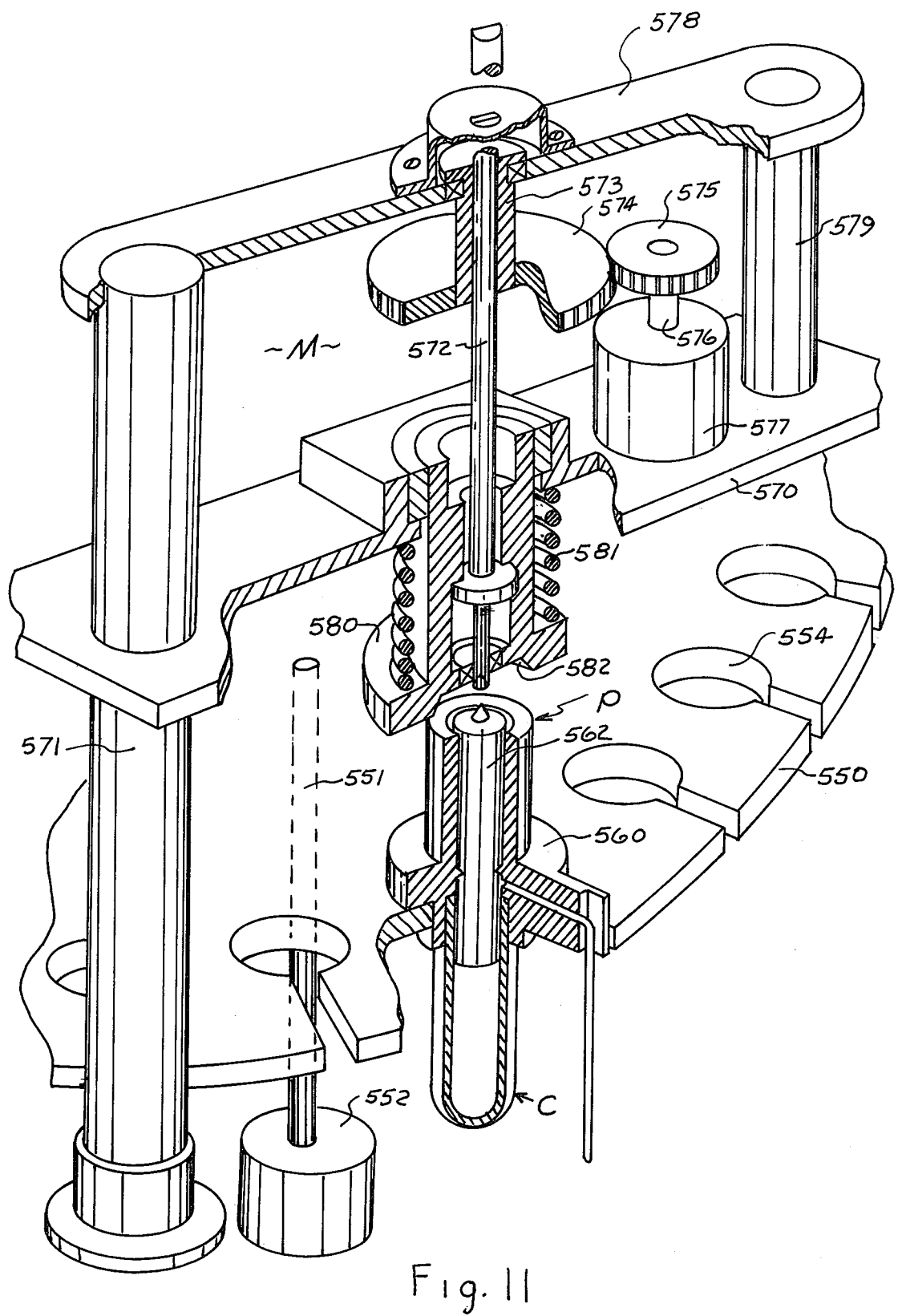

The apparatus at the sample fluid dispensing station S is shown in FIGS. 10 and 11 and includes a turntable 550 disposed in a generally horizontal plane and rotatably movable in stepped fashion about a suitable axis (shaft 551) by means of motor 552. Turntable 550 is provided with a plurality of axially spaced keyhole slots 554 into each of which is disposed a container C of a patient's body fluid to be tested.

As seen in FIG. 10, when it is desired to test a particular patient's fluid sample, his container C which carries his identification is stepped by the turntable 550 around to the dispensing position P, as shown. Fluid dispensing mechanism M, FIG. 11, is located at dispensing position P and operable to dispense a predetermined sample of the body fluid from container C into the process serum cup 508.

As seen in FIG. 11, the container C is generally cylindrical and contains a predetermined quantity of the patient's body fluid. Container C is securely mounted in an upstanding barrel 560. A displacement cylinder 562 of predetermined diameter is slidably disposed in barrel 560 and movable into the container C to displace a predetermined volume of fluid from said container C, through spout N and into the process or serum cup 508. For this purpose, the dispensing mechanism is carried on platform 570 that is supported on post 571 as to extend over the turntable 550.

Dispensing rod 572 is journalled in bearing member 573 which mounts a drivable gear 574 disposed in meshing engagement with drive gear 575 mounted on the end of shaft 576 of motor 577, the latter being also carried on the platform 570.

Bearing member 573 is mounted within top plate 578 supported above platform 570 by aforementioned post 571 and post 579 to thus provide for accurate vertically downward actuation of the dispensing rod 572.

Dispensing rod 572 projects into and through bulkhead member 580, the latter being resiliently suspended downwardly from platform 570.

To dispense a predetermined quantity of body fluid from container C, the platform 570 is lowered on post 571 to bring the annular seat 582 of bulkhead member 580 into seating engagement with the upper end of the barrel 560 against the resistance of coil spring 581 to thereby provide a fluid seal therebetween.

Motor 577 is then energized to rotate dispensing rod 572 and move its lower end into engagement with the upper tip of the displacement cylinder 562 effective to drive said cylinder downwardly, as viewed in FIG. 11, through the container C. As a result, a predetermined quantity of the body fluid in said container C is displaced outward through connecting spout tube N into the serum cup 508 disposed therebelow. The displacement cylinder 562 is provided with an accurate diameter as to provide a small clearance between it and the container wall and thereby enable the body fluid to flow therethrough and into the connecting spout N and serum cup 508.

Platform 570 is thereafter raised and lifts the dispensing rod 572 and bulkhead 580 upwardly to ready the dispensing mechanism for the next dispensing operation.

The carriage D may then be actuated to carry the serum cup 508 along the processing path to the next stations in the preselected process of testing the patient's sample.

Referring to FIG. 9, the serum cup storage magazine and dispenser unit is illustrated. In its present form it includes a storage bin 600 mounted in an upright position on plate 601 and into which a plurality of serum cups S are stacked on their side with the open-necked end n of each lying adjacent the side wall 600a of said bin. The bottom of the storage bin is defined by a flat plate 603 slidably carried within slot 604 formed on each bin side wall 600a and which in its closed position forms a base wall for the bin to support the serum cup stack thereon. Upon sliding the plate 603 to the right as viewed in FIG. 9, the bin communicates with the serum cup dispenser chamber 605 into which the serum cups may fall again in stacked relation to await their being individually dispensed therefrom.

The dispenser chamber 605 is provided at its left end, as viewed in FIG. 9, with an arcuate wall 607 which extends downwardly and inwardly toward the center of the chamber. A similarly shaped arcuate wall 609 is provided on the right end of the chamber as seen in FIG. 9 and is located thereon so that its lowermost edge is on a plane above the adjacent lower edge of arcuate wall 607.

Sprocket 610, having a plurality of axially spaced and axially extending recesses 612 formed therein, is rotatably mounted on shaft 613 within the dispenser chamber 605 between arcuate walls 607 and 609. Motor 614 is drivingly connected to shaft 613 and is operable to incrementally rotate or step the sprocket 610, clockwise as viewed in FIG. 9, to sequentially position one of the recesses 612 thereon to permit one of the serum cups to be picked up and deposited therein. As seen in FIG. 9, three of said cups are deposited in the sprocket recesses and are being carried thereby to a position adjacent to and over chute 620.

Chute 620 is formed with a back wall consisting of an upper wall section 621 extending upwardly and rearwardly toward the sprocket 610 and a lower vertical wall section 622.

Disposed forwardly of or to the right of the back wall, as viewed in FIG. 9, is a ramp 625 having an upper section 626 extending angularly downwardly and inwardly toward a vertical wall section 627 which abuts the vertical wall section 622 of the back wall to form a corner 630.

When the serum cup identified at "c" in FIG. 9 is carried by the sprocket 610 to the position illustrated, it falls by gravity out of the sprocket recess and toward the chute 620 such that the neck-end (n) strikes the ramp wall 626, whereby it pivots counterclockwise as seen in FIG. 9, from an approximate horizontal plane to a vertical plane and lands upright, as illustrated at "b", on the upper flat surface 631 of dispensing block member 632.

Block member 632 is reciprocally slidably movable on base member 634, between the serum cup receiving position as depicted in FIG. 9, forwardly or to the right as viewed therein, to a serum cup dispensing position where a serum cup is located at position "p" on shelf 640.

To accomplish the reciprocal movement, a motor 645 is mounted on side wall 646 of the bin housing 600, and a circular disc 647 is axially carried on the motor shaft 648. A lever 649 has its one end attached to the peripheral edge of the disc and its opposite end attached to the block member 632. Actuation of the motor 645 and rotation of the disc 647 reciprocates the lever 649 and attached block member 632 between its aforementioned positions.

As viewed in FIG. 9, block member 632 is at its rearmost serum cup receiving position whereat the serum cup "d" has fallen out of the chute pocket 630 and onto the upper surface of base member 634 ahead of the block member 632.

Thereafter, actuation of motor 645 slides block member 632 forwardly or to the right, as viewed, to slide serum cup "c" between a pair of fingers 652 which slightly grasp the necked end of said serum cup therebetween. Movement of the block member 632 is continued until the serum cup reaches position "p" and is placed onto shelf 640 at which time the block member 632 is then pulled rearwardly back to its rearmost position as shown in FIG. 9. During forward and rearward movement of the block member 632 during this dispensing cycle the next-to-be dispensed serum cup "b" slides upon the top surface of said member while remaining in the chute corner 630. And, upon the block member 632 reaching its rearmost position, said next-to-be dispensed cup drops onto the upper surface of base member 634 in front of said block member to await the next dispensing cycle.

When a serum cup is to be dispensed, the carriage D is moved along the processing path and positioned directly in front of the shelf 640 so that the resilient fingers 540 (FIG. 10) of the holder H are positioned over the shelf 640 and directly forwardly of the fingers 652.

As the block member 632 slides the serum cup onto the shelf 640 (FIG. 9) position "p" the necked-end "n" of said cup is grasped between said fingers 540 and retained therein as the block member 632 is reciprocated rearwardly to return to its FIG. 9 position.

With the serum cup thus captured within the container D, it may then be moved to the sample fluid dispensing station P, FIG. 10, to receive a sample of said fluid for test.

Figure 12:
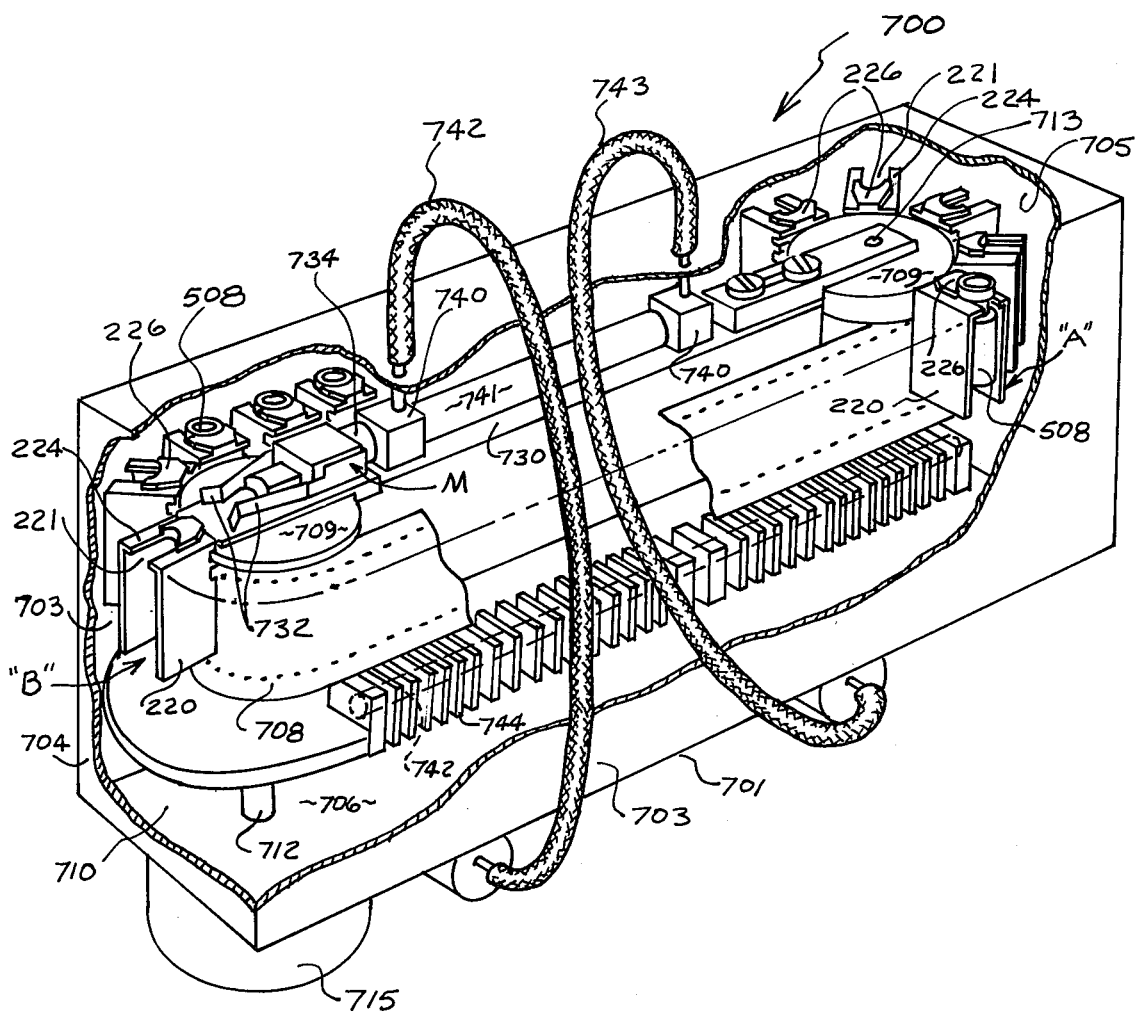

FIG. 12 illustrates an alternate embodiment of incubator station identified in its entirety at 700 and which may be disposed along the processing path in the position occupied by the container storage zone 82 in the aforedescribed third zone of apparatus.

In its alternate structure, a generally rectangular shaped housing 701 is disposed alongside the processing path as defined by guideway 12 and is formed with opposing elongated side walls 703, front wall 704, rear wall 705 and bottom wall 706.

An endless belt 708 is journalled around spaced sprockets 709 so as to extend longitudinally centrally through the housing chamber 710. Sprockets 709, in turn, are rotatably carried on stub shafts 712, 713 which are mounted on the bottom wall 706 adjacent the end walls 704, 705 and extending vertically upwardly therefrom.

Motor 715 attached to the underside of the bottom wall 706 is drivingly connected to stub shaft 712 and controlled by the system control means 134 to rotate the endless belt 708 in a manner to be further described.

A plurality of generally U-shaped storage receptacles 220 are mounted on the outside surface of the endless belt 708 in spaced relation therearound. Each of said receptacles is provided with a slot 221 formed in the top wall to define spaced parallel extending shoulders 224.

Each of said receptacles is carried by the endless belt through the housing chamber 710 and is intended to receive and temporarily store a serum cup 508 therein. As shown at position "A", in FIG. 12, the serum cup 508 is disposed within its receptacle so that its necked open end seats upon the upper wall shoulders 224 and abuts against raised abutment 226.

The front wall 704 of the housing 701 is formed with an opening (not shown) which is directly in front or to the left, as viewed in FIG. 12, of a receptacle entrance and dispensing position "B". In this position, a serum cup 508 may be carried by one of the carriages D along guideway 12 and directly in frong of the housing opening and an ejector mechanism M ma then be actuated to remove the serum cup from the carriage holder H and deposit the same into the receptacle. Likewise, the ejector mechanism M may be operable to remove a serum cup from its receptacle at position "B" and to deposit said cup onto the carriage holder H.

To accomplish this, the ejector mechanism M is mounted on the central hub 730 of the endless belt assembly adjacent sprocket 709 carried on drive shaft 712. Said mechanism M has a picker device comprising a pair of spring or resilient fingers 732 which are attached to the end of solenoid operated plunger 734. Coil elements 740 disposed at opposite ends of the plunger housing 741 are connected in circuit by conductors 742, 743 to the control means 134 and are operable to reciprocate the plunger 734 over the receptacle at position "B".

In operation, with an empty receptacle located at position "B", the carrier D having a serum cup containing a patient's sample fluid may be moved along the guideway 12 to locate the serum cup holder H directly in front of the housing opening and opposite this receptacle. Thereafter, the solenoid is actuated to extend the plunger 734 to the left as viewed in FIG. 12 over and in front of the receptacle until the resilient fingers 732 embrace the upper end of the serum cup in holder H. The solenoid is then reversibly actuated to retract the plunger 734 to the right whereby the serum cup is removed from the holder H and deposited within the receptacle at position "B".

The motor 715 may then be energized by control means 134 to drive the endless belt 708 and carry said receptacle and serum cup into the housing chamber 710 for any predetermined period of incubation. The motor may be maintained energized until the next empty receptacle is located at position "B" or until the next receptacle already carrying a serum cup and whose incubation period is complete is located at said dispensing position "B" to await removal of the same and onto the holder H of carriage D.

The temperature of the housing chamber 710 is preferably maintained at a suitable constant temperature by a heating unit controllable by the control means 134 comprising a calrod 742 disposed centrally within radiator 744 which is disposed within said chamber and extending longitudinally therethrough.

With this heater assembly, the incubator chamber 710 may be maintained at any desired temperature.

The several variations represented by the apparatus are only examples of the invention from which it will follow that considerable variation is capable of being made without in any way departing from the spirit or scope of the invention as defined in the appended claims. These variations are feasible not only in modifications of the overall system but in the different forms that the individual components may take.

What is claimed is:

1. Automated apparatus for processing fluids such as blood and the like for obtaining information relating to the physical and/or chemical properties thereof and providing a readout representative of such information, the apparatus being capable of performing different processes on different fluids not necessarily having the same processing time which comprises:

A. means defining a single processing path for said apparatus; means for supporting a plurality of containers each adapted to carry therein a sample of fluid to be processed along said path, any one process perhaps requiring a different processing procedure, each of the containers having respective indicia means identifying the sample adapted to be carried thereby and its processing procedure, the containers being arranged in said supporting means in a random order;

B. transport means for removing a first container from the supporting means, reading its indicia means and moving the same along said processing path in a first preselected pattern according to the processing procedure identified on the indicia means for said first container;

C. at least one processing means stationed along said processing path to define said preselected first pattern, the transport means and processing means having cooperating structure enabling the transport means to stop said first container in said path and at the processing means in said preselected first pattern and to subject the container to the effects of said processing means, the cooperating structure including means to permit the said container to be removed from said transport means and to be translated into operative association with at least said one processing means in said first pattern and returned to said transport means; and D. control and programming means connected with said apparatus and effective to operate the transport means along said path operable to take a second container and to locate the same in at least a second processing means in said path defining a part of a second preselected pattern according to the processing procedure identified on the indicia means on said second container, the movement of said second container to said second processing means occurring during the period when said one container in said first pattern is at said one processing means being thus effective to utilize the time during said one container is at said one processing means for commencing, completing or continuing the processing of said second container according to the time available therefor, said control and programming means including a memory having the processing procedure data stored therein and acting to monitor the procedures being performed upon consecutively processed containers and the sample adapted to be contained therein in a manner which permits the transport means to move a plurality of containers through at least partially a plurality of preselected patterns during the same period of time and on a time sharing basis between said plurality of preselected patterns and which thus utilizes the minimum processing time possible for each said sample without regard to the processing time of other said samples.

2. The apparatus as claimed in claim 1 in which one of the processing means comprises storage means for retainining a container for a predetermined period of time as a part of a certain pattern and the cooperating structure is capable of depositing said last-mentioned container in said storage means and removing same after said predetermined period of time.

3. The apparatus as claimed in claim 1 in which said moving means comprise a carriage and a guideway, the guideway defining the processing path, said cooperating structure including a sample container reciprocating device mounted on said carriage and having means for holding engaging and releasing a container.

4. The apparatus as claimed in claim 1 in which one of the processing means comprises testing means for testing said samples when said moving means stops containers carrying samples at the testing means.

5. The apparatus as claimed in claim 1 in which one of said processing means comprises testing means having a plurality of testing stations, each testing station capable of applying a different test to a sample and the control and programming means being capable of camming said moving means to stop containers at all of said testing stations but being effective to stop a single container at a particular testing station when the pattern of the indicia means of said single container requires the testing of said particular testing station.

6. The apparatus as claimed in claim 1 in which one of said processing means includes reagent-adding means and the cooperating structure is capable of moving a container into association with said reagent-adding means for a sufficient time to receive reagent therefrom and thereafter to remove said last-mentioned container from said association.

7. The apparatus as claimed in claim 1 in which the samples are adapted to be contained in the containers of said supporting means prior to removing the containers therefrom and reading the indicia means thereof.

8. The apparatus as claimed in claim 1 in which the containers of said supporting means are initially empty and said apparatus includes storage means for carrying a quantity of sample liquid and means for transferring an aliquot of said sample liquid smaller than said quantity from storage means to each container after it has been removed from said supporting means and at earliest when its indicia means is read.

9. The apparatus as claimed in claim 1 in which the containers of said supporting means are initially empty and means are provided for holding a supply container with a quantity of fluid therein adapted to be transferred in an aliquot to each of the empty containers to provide a sample of said fluid in each of said containers, said supply container having second indicia means different from the other indicia means, said apparatus includes storage and metering means, and said container removing means are arranged initially to remove the supply container from its holding means to enable its second indicia means to be read, the storage and metering means being arranged thereafter to remove the fluid from said supply container and to meter an aliquot and transfer the same to each container after the respective container has been removed from said supporting means and its indicia means read.

10. The apparatus as claimed in claim 2 in which patterns at least one of which includes deposit of a container in said storage means are effected on a time sharing basis, said control and programming means and memory being capable of operating said removing, reading and moving means and the cooperative structures in a manner to utilize the delay time during which one container is in said storage means for commencing, completing or continuing the processing of another container according to the time available therefor.

11. The apparatus as claimed in claim 2 in which another of said processing means includes reagent-adding means and the cooperating structure is arranged to move a container into association with said reagent-adding means for a sufficient time to receive reagent therefrom and thereafter to remove said last-mentioned container from said association.

12. The apparatus as claimed in claim 2 in which said storage means include a plurality of stalls at different stations along said path, each stall having temperature-control means so that any container which is moved into a stall will be subjected to an individual temperature, the deposit of a container comprising the moving of same into a stall and leaving the same therein.

13. The apparatus as claimed in claim 2 in which one of the processing means comprises testing means for testing said samples when said moving means stops containers carrying samples at the testing means.

14. The apparatus as claimed in claim 2 in which one of said processing means comprises testing means having a plurality of testing stations, each testing station capable of applying a different test to a sample and the control and programming means being capable of causing said moving means to stop containers at all of said testing stations but being effective to stop a single container at a particular testing station when the pattern of the indicia means of said single container requires the testing of said particular testing station.

15. The apparatus as claimed in claim 4 in which another of said processing means comprise readout means for recording the data produced by said testing means, said apparatus including means to enable the readout means to receive said data and respond to the indicia means of a container which has had its sample tested to produce such data.

16. The apparatus as claimed in claim 5 in which another of said processing means comprise readout means for recording the data produced by said testing means, said apparatus including means to enable the readout means to receive said data and respond to the indicia means of a container which has had its sample tested at one of said testing stations to produce the specific data from only said one testing station when said container is stopped at said readout means.

17. The apparatus as claimed in claim 9 in which the storage and metering means include a snorkel and snorkel moving means, the snorkel adapted to be inserted into said containers or removed therefrom as the case may be for respectively withdrawing or dispensing sample fluid.

18. The apparatus as claimed in claim 10 in which another of said processing means includes reagent-adding means and the cooperating structure is arranged to move a container into association with said reagent-adding means for a sufficient time to receive reagent therefrom and thereafter to remove said last-mentioned container from said association, said cooperating structure being capable of moving and removing said last-mentioned container during said delay time if sufficient.

19. The apparatus as claimed in claim 11 in which said reagent-adding means have a plurality of reagent-adding stations each being arranged to deliver a different reagent to a container and the control and programming means are effective to cause the moving means to bring a container into association with a particular reagent-adding station of said reagent-adding means in accordance with a pattern which is identified with that particular container in the indicia means thereof.

20. The apparatus as claimed in claim 11 in which said reagent-adding means have a plurality of reagent-adding stations each being arranged to deliver a different reagent to a container and the control and programming means are effective to cause the moving means to bring a container into association with a particular reagent-adding station of said reagent-adding means in accordance with a pattern which is identified with that particular container in the indicia means thereof.

21. The apparatus as claimed in claim 11 in which still another of said processing means comprises testing means for testing said samples when said moving means stops containers carrying samples at said testing means.

22. The apparatus as claimed in claim 11 in which still another one of said processing means comprises testing means having a plurality of testing stations, each testing station capable of applying a different test to a sample and the control and programming means being capable of causing said moving means to stop containers at all of said testing stations but being effective to stop a single container at a particular testing station when the pattern of the indicia means of said single container requires the testing of said particular testing station.

23. The apparatus as claimed in claim 12 in which the control and programming means is effective to cause the moving means to bring the container adjacent any particular stall as called for by the indicia means of the container moved by said moving means and to further cause the cooperating structure to move the last container into said particular stall and leave it there for a predetermined period of time also called for by the indicia means of said last container before removing same therefrom.

24. The apparatus as claimed in claim 18 in which said reagent-adding means have a plurality of reagent-adding stations each being arranged to deliver a different reagent to a container and the control and programming means are effective to cause the moving means to bring a container into association with a particular reagent-adding station of said reagent-adding means in accordance with a pattern which is identified with that particular container in the indicia means thereof.

25. The apparatus as claimed in claim 18 in which still another one of said processing means comprises testing means for testing samples when said moving means stops containers carrying samples at the testing means.

26. The apparatus as claimed in claim 19 in which still another one of said processing means comprises testing means having a plurality of testing stations, each testing station capable of applying a different test to a sample and the control and programming means being capable of causing said moving means to stop containers at all of said testing stations but being effective to stop a single container at a particular testing station when the pattern of the indicia means of said single container requires the testing of said particular testing station.

27. The apparatus as claimed in claim 19 in which still another of said processing means comprises testing means for testing samples when said moving means stops containers carrying samples at said testing means.

28. The apparatus as claimed in claim 24 in which the storage means include a plurality of stalls at different stations along said path, each stall being maintained at respective certain temperatures including at least one temperature which may not be the same as another, so that any container which is moved into a stall will be subjected to the certain temperature of said stall, the deposit of a container comprising the moving of same into a stall and leaving same therein for a particular delay time, at least one reagent added requiring a different delay time than another.

29. The apparatus as claimed in claim 24 in which still another one of said processing means comprises testing means for testing samples when said moving means stops containers carrying samples at the testing means.

30. The apparatus as claimed in claim 28 in which still another one of said processing means comprises testing means for testing samples when said moving means stops containers carrying samples at the testing means.

31. The apparatus as claimed in claim 25 in which the testing means have a plurality of testing stations, each testing station capable of applying a different test to a sample and the control and programming means being capable of causing said moving means to stop containers at all of said testing stations but being effective to stop a single container at a particular testing station when the pattern of the indicia means of said single container requires the testing of said particular testing station.

32. The apparatus as claimed in claim 29 in which the testing means have a plurality of testing stations, each testing station capable of applying a different test to a sample and the control and programming means being capable of causing said moving means to stop containers at all of said testing stations but being effective to stop a single container at a particular testing station when the pattern of the indicia means of said single container requires the testing of said particular testing station.

33. The apparatus as claimed in claim 30 in which the testing means have a plurality of testing stations, each testing station capable of applying a different test to a sample and the control and programming means being capable of causing said moving means to stop containers at all of said testing stations but being effective to stop a single container at a particular testing station when the pattern of the indicia means of said single container requires the testing of said particular testing station.

34. The apparatus as claimed in claim 25 in which still another of said processing means comprise readout means for recording the data produced by said testing means, said apparatus including means to receive said data and respond to the indicia means of a container which has had its sample tested to produce such data.

35. The apparatus as claimed in claim 29 in which still another of said processing means comprise readout means for recording the data produced by said testing means, said apparatus including means to receive said data and respond to the indicia means of a container which has had its sample tested to produce such data.

36. The apparatus as claimed in claim 30 in which still another of said processing means comprise readout means for recording the data produced by said testing means, said apparatus including means to receive said data and respond to the indicia means of a container which has had its sample tested to produce such data.

37. The apparatus as claimed in claim 25 in which another of said processing means comprise readout means for recording the data produced by said testing means, said apparatus including means to enable the readout means to receive said data and respond to the indicia means of a container which has had its sample tested at one of said testing stations to produce the specific data from only said one testing station when said container is stopped at said readout means.

38. The apparatus as claimed in claim 29 in which another of said processing means comprise readout means for recording the data produced by said testing means, said apparatus including means to enable the readout means to receive said data and respond to the indicia means of a container which has had its sample tested at one of said testing stations to produce the specific data from only said one testing station when said container is stopped at said readout means.

39. The apparatus as claimed in claim 30 in which another of said processing means comprise readout means for recording data produced by said testing means, said apparatus including means to enable the readout means to receive said data and respond to the indicia means of a container which has had its sample tested at one of said testing stations to produce the specific data from only said one testing station when said container is stopped at said readout means.

40. Automated apparatus for processing fluids such as blood and the like for obtaining information relating to the physical and/or chemical properties thereof and providing a readout representative of such information, the apparatus being capable of performing different processes on different fluids and the processes being effected by said apparatus not necessarily having the same processing time, said apparatus comprising:
  A. means defining a single processing path for said apparatus,
  B. sample container supply means including support structure for holding a plurality of sample containers in position to be removed from said supply means for processing along said path according to predetermined procedures, each container adapted to carry a different sample to be processed, the time of processing not necessarily being the same for each procedure, each container having access means to enable liquid to be withdrawn from or inserted into the interior of said container and each said container also carrying indicia means having at least sample identification and a test code thereon with the code being individual to a particular one of said predetermined procedures;
  C. transport means for said containers including a container-carrying carriage, said path defining means including a guideway, means for driving the carriage along said path and confined to said guideway, said carriage and guideway having cooperating position-identifying means for providing electrical signals for identifying the location of the carriage along the guideway at all times;
  D. a plurality of zones and a station located along the guideway and including:
    i. an initial indicia means reading zone having at least one position provided with test code reading means, said test code reading means serving when enabled to provide signals representative of said test code, said sample container supply means being at said initial indicia means reading zone,
    ii. a reagent-adding zone having at least one position provided with reagent adding means thereat,
    iii. a testing zone having at least one position with testing means thereat and
    iv. a final indicia means reading station having apparatus for providing a readout of testing information responsive to said indicia means;
  E. said carriage, sample supply means, initial reading means, testing means and readout apparatus having cooperative structure including a container-reciprocating device connected with said carriage for translating a container carried by said carriage angularly away from or toward the said path, said cooperative structure being effective
    i. to enable a container to be withdrawn from said supply means and moved onto said carriage and its indicia means to be read by said reading means while said carriage is at said initial indicia means reading zone,
    ii. to enable said last-mentioned container to be translated into association with said reagent-adding means and to have reagent inserted into the interior of said container through said access means and thereafter the container translated back to said carriage while said carriage is at said reagent-adding zone,
    iii. to enable the withdrawing of liquid from the interior of said last-mentioned container through said access means when said carriage is at said testing zone, and the testing means including liquid withdrawing means and testing signal producing means responsive to the presence of the liquid thus withdrawn, and
    iv. to enable the readout apparatus to provide a readout responsive to said last-mentioned testing signal when the carriage is at said final indicia means reading station, said readout apparatus having means for reading the indicia means and providing a call-up signal individual to sample identification and test code thereon,
  F. means for removing said indicia means and container from said carriage for subsequent disposition after operation of said readout apparatus,
  G. means for driving the carriage along said path to said initial indicia means reading zone and to a location for withdrawing a second container and to locate said second container at a second processing means in said path defining a part of second preselected processing pattern, the movement of said second container to said second processing means occurring during the period when said one container in said first pattern is at said processing means being thus effective to utilize the time during said one container is at said one processing means for commencing, completing or continuing the processing of said second container according to the time available therefor, H. means for programming and controlling the operation of said apparatus and including circuitry for permanently and temporarily storing electrical information, said electrical information including command signal data for ordering the performance of said predetermined procedures in response to the respective test codes individual to said procedures, the said position-identifying electrical signals, command signal date for controlling the operation of said cooperative structure and the timing thereof and for storing and calling up the testing signals responsive to the operation of the readout apparatus, said apparatus continuously performing the withdrawal, reading, reagent-adding, testing and readout in a timed sequence for each sample in accordance with the said test-code individual to said last-mentioned sample and operating said transport means and cooperative structure while so performing for all of the respective samples which may be carried by said containers.

41. Automated apparatus as claimed in claim 40 in which said plurality of zones includes a storage zone having at least one storing position thereat capable of receiving and holding a container therein, said cooperative structure also being effective to enable a container to be translated into said storing position from said carriage while said carriage is at said storage zone, left remaining in said storage zone and removed therefrom after a delay time established by said programming and controlling means.

42. Automated apparatus as claimed in claim 40 in which the initial indicia means reading zone has in addition sample fluid removing, storing and dispensing means thereat, the containers of said supply means being initially empty but for a carrier container, the removing, storing and dispensing means being effective to remove the sample fluid contained in the carrier container, store the same and dispense an aliquot thereof to each of the empty containers removed from the supply means to said test code reading means.

43. The apparatus as claimed in claim 41 in which said carriage is adapted to be moved by said transport means away from said storage zone during said delay time and returned at the end of said delay time to remove the container from said storing position for further processing of the same.

44. The apparatus as claimed in claim 43 in which said storage zone has a plurality of storing positions and at least two of said storing positions have means for maintaining different temperatures respectively therein to affect containers stored therein.

45. The apparatus as claimed in claim 44 in which said reagent-adding zone has a plurality of reagent-adding stations, each having means for inserting into a container disposed in association therewith a reagent different from that of another reagent-adding station.

46. The apparatus as claimed in claim 44 in which said testing zone has a plurality of testing positions with different testing apparatus in each position.

47. The apparatus as claimed in claim 40 in which said transport means includes a second container-carrying carriage on the same guideway as the first carriage, means for driving the additional carriage along the guideway overlapping the extent of travel of the first carriage and said programming and controlling means capable of synchronizing the travel of said carriages to maintain an interferencefree relationship therebetween, means to enable the second carriage to perform that function which would otherwise be performed by said first carriage on an occasion when the delay time established by said program and controlling means is insufficient to permit performance of that function by said first carriage.

48. In automated apparatus as is defined in claim 1 and wherein at least several of the preselected processing patterns are located in at least partial overlapping relation to each other on said path effective to provide said transport means for reciprocal movement along said path in effecting the processing of the containers in said several processing patterns.

49. Apparatus as defined in claim 3 and wherein a container is releasably connected to said container reciprocating device to and from at least said one processing means, said container having means permitting it to be slidably movable by and relative to said reciprocating device for disposition at said one processing means.

50. Apparatus as defined in claim 49 and wherein the container is provided with a generally rectangular body, channel means in said body and rail means at said processing means extending into said channel means and supporting said container as it is moved toward said processing means by said reciprocating device.

51. Apparatus as defined in claim 50 and wherein the container is provided with a generally rectangular body adjacent one end of which has fluid retaining means.

52. Apparatus as defined in claim 51 and wherein the container is provided with a generally cylindrical fluid retainer depending from the container body, and means in said body to enable access into said retainer for presentation of a sample quantity of fluid therefrom and to said processing means.

53. Apparatus as defined in claim 52 and wherein the container is provided with upstanding abutment means coacting with latch means at said processing means effective to releasably retain the container at said processing means.

54. Automated apparatus for processing fluids such as blood and the like for obtaining information relating to the physical and/or chemical properties thereof and providing a readout representative of such information, the apparatus being capable of performing different processes on different fluids not necessarily having the same processing time which comprises:

A. means defining a single processing path for said apparatus; means for supporting a plurality of containers each adapted to carry therein a sample of fluid to be processed along said path, any one process perhaps requiring a different processing procedure, the containers being arranged in said supporting means in a random order;

B. transport means for removing a first container from the supporting means and moving the same along said processing path in a first preselected pattern according to the processing procedure for said first container;

C. at least one processing means stationed along said processing path to define said preselected first pattern, the transport means and processing means having cooperating structure enabling the transport means to stop said first container in said path and at the processing means in said preselected first pattern and to subject the container to the effects of said processing means, the cooperating structure including means to permit the said container to be removed from said transport means and to be translated into operative association with at least said one processing means in said first pattern and returned to said transport means; and D. control and programming means connected with said apparatus and effective to operate the transport means along said path operable to take a second container and to locate the same in at least a second processing means in said path defining a part of a second preselected pattern according to the processing procedure for said second container, the movement of said second container to said second processing means occurring during the period when said one container in said first pattern is at said one processing means being thus effective to utilize the time during said one container is at said one processing means for commencing, completing or continuing the processing of said second container according to the time available therefor, said control and programming means including a memory having the processing procedure data stored therein and acting to monitor the procedures being performed upon consecutively processed containers and the sample adapted to be contained therein in a manner which permits the transport means to move a plurality of containers through at least partially a plurality of preselected patterns during the same period of time and on a time sharing basis between said plurality of preselected patterns and which thus utilizes the minimum processing time possible for each said sample without regard to the processing time of other said samples.

55. The apparatus as claimed in claim 54 and wherein the means for supporting a plurality of containers comprises a magazine having a housing formed with a chamber for storing a plurality of the containers, dispensing means in communication with said chamber and operable to remove a single container from said chamber and to locate the same alongside the processing path in an upright position capable of receiving a fluid sample therein.

56. The apparatus as claimed in claim 55 and wherein the dispensing means comprises a sprocketed cylinder having recesses formed therein each adapted to receive a container from said chamber, and means located adjacent to said cylinder engageable with each container as it is released from said cylinder recess to position said container in an upright position capable of receiving and retaining a fluid sample therein.

57. The apparatus as claimed in claim 56 and wherein the dispensing means includes pusher means engageable with the released container and to move the same to a position adjacent to the processing path whereat it is picked up by the carriage movable along said path.

58. The apparatus as claimed in claim 54 and wherein fluid sample dispensing means is positioned adjacent the processing path and the container transport means is operable to carry an empty container to said dispensing means and to receive a fluid sample therefrom.

59. The apparatus as claimed in claim 58 and wherein the dispensing means comprises a turntable having means thereon for carrying a plurality of containers each adapted to carry a fluid sample of a preselected patient's body fluids, and means for dispensing a predetermined volume of the fluid sample into a container carried on the transport means.

60. The apparatus as claimed in claim 54 and wherein one of the processing means stationed along the processing path comprises an incubator chamber for temporarily storing a plurality of containers therein.

61. The apparatus as claimed in claim 60 and wherein conveyor means movably disposed in the incubator chamber is operable to temporarily carry a plurality of containers therein.

62. The apparatus as claimed in claim 61 and wherein the conveyor means is provided with a plurality of receptacles each of which is adapted to receive a container therein.

63. The apparatus as defined in claim 54 and wherein dispensing means in the incubator chamber is operable to dispense a container to and from the transport means and said chamber.

* * * * *